US010407687B2

(12) United States Patent
Butler et al.

(10) Patent No.: US 10,407,687 B2
(45) Date of Patent: Sep. 10, 2019

(54) ***BRASSICA NAPUS* SEED SPECIFIC PROMOTERS IDENTIFIED BY MICROARRAY ANALYSIS**

(71) Applicant: Dow AgroSciences LLC, Indianapolis, IN (US)

(72) Inventors: Holly Jean Butler, Indianapolis, IN (US); Scott Alan Bevan, Indianapolis, IN (US); Cory M. Larsen, Zionsville, IN (US); William Moskal, Indianapolis, IN (US); Delkin Orlando Gonzalez, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 7 days.

(21) Appl. No.: 15/542,037

(22) PCT Filed: Dec. 28, 2015

(86) PCT No.: PCT/US2015/067584
§ 371 (c)(1),
(2) Date: Jul. 6, 2017

(87) PCT Pub. No.: WO2016/111859
PCT Pub. Date: Jul. 14, 2016

(65) Prior Publication Data

US 2018/0002714 A1 Jan. 4, 2018

Related U.S. Application Data

(60) Provisional application No. 62/100,389, filed on Jan. 6, 2015.

(51) Int. Cl.
*C12N 15/82* (2006.01)
*C07K 14/415* (2006.01)

(52) U.S. Cl.
CPC ........ *C12N 15/8234* (2013.01); *C07K 14/415* (2013.01)

(58) Field of Classification Search
None
See application file for complete search history.

(56) References Cited

U.S. PATENT DOCUMENTS

| | | | | |
|---|---|---|---|---|
| 2010/0263088 | A1 | 10/2010 | Bauer et al. | |
| 2011/0113510 | A1 | 5/2011 | Bauer et al. | |
| 2012/0022235 | A1 | 1/2012 | Ruezinsky et al. | |
| 2013/0104257 | A1 | 4/2013 | Gupta et al. | |
| 2014/0230087 | A1 * | 8/2014 | Hartig | C12N 15/8216 800/278 |

FOREIGN PATENT DOCUMENTS

WO 2016111859 7/2016

OTHER PUBLICATIONS

Kim Y.et al. A 20 nucleotide upstream element is essential for the nopaline synthase (nos) promoter activity. Plant Mol Biol. Jan. 1994;24(1):105-17. (Year: 1994).*

Sullivan et al. Mutational analysis of the DST element in tobacco cells and transgenic plants: identification of residues critical for mRNA instability. RNA. Apr. 1996;2(4):308-15. (Year: 1996).*

NCBI GenBank Accession No. EF584012-1, *Brassica rapa* clone P2-9 hypothetical protein genes, complete cds; hypothetical protein gene, partial cds: and hypothetical protein genes, complete cds, Jul. 10, 2007.

Search Report and Written Opinion for PCT/US2015/067584, dated Apr. 19, 2016.

* cited by examiner

*Primary Examiner* — Cynthia E Collins

(57) ABSTRACT

Provided are constructs and methods for expressing a transgene in plant cells and/or plant tissues using gene regulatory elements obtained from *Brassica napus*.

20 Claims, 3 Drawing Sheets

Specification includes a Sequence Listing.

SEQUENCE LISTING

```
<160> NUMBER OF SEQ ID NOS: 12

<210> SEQ ID NO 1
<211> LENGTH: 1429
<212> TYPE: DNA
<213> ORGANISM: Brassica napus

<400> SEQUENCE: 1

caacaaaaat gcactttttc gccaaaaata catttttctt caaaaaccgc aaaaatattt     60

tctgccaaac ccgtaaaaat actatttttc tgccgaaacg taaaaaaaaa tattttaatt    120

attttattaa caagtccact tggatgtaga tgaaaattta aaaaatgaaa agcaaacgaa    180

catagttgca ttcagatgat tcatctggat gcatggacga aatgaagaaa cgaacaacac    240

ccatatagag catctggata agacatctag atggatcatt acaaaagaac agggcctaaa    300

catgtgagat gtttgaagca atcagtcaaa agtaaccacc aaatcgaatt atgaaagcgt    360

tgattggatg gacaagttta acaaccattg tttgattgga caacgccgtt atctaaactt    420

ttagtgtgct gtgtacatca ttactatgaa tcagttagtt aaaaatatta tggtcagtga    480

atgacagtaa gattacttca gaacttgaga gatttaccgc aaaaagaaac acaataacgc    540

gtaggaaaaa tatcctctgt tttttgcaat tattctcgta gatttggtta tcagtaggta    600

tcacgtttta caaaaataga attacaatac atgccgcaag aaaaagactt tctcttttta    660

atttccccaa tttggttatc agtattcagt aagtttcaca tttttacaaa aatataaatt    720

aaaatacata ctgcaagaaa aatacttttt taatttcgcc aatttggtta tcagtagttt    780

tcacattttt acaaaaatat aattaaaata taaactgcaa caaaaagact tatcttttta    840

atttccccaa tttggttatc agtattcagt aggtttcaca tttacaaaaa tattattaaa    900

atacatactg caagaaacat accttttaa tttcgccaat ctggttatca gtagttttca    960

catttttaca aaaatagaat taaaatacaa actgcaacaa aaagacttat ctttttaatt   1020

tccaccaata agttatttat ttatttaatc ctcccgtgag gaaaaagaca agattgagga   1080

tgaatatacg taactgaaaa ttgaggaaac agagccatca acctttcaac acggatgatc   1140

atcatcatca ctctctgccg cctttaaata gaaaccaaca aagacattct tgagcccaca   1200

ctcactcctt tcctatttct tcgctttgcg tgccttcctt ccttcttatc tacttgtatc   1260

ccacaaaaag ctacttaata ccatttaata aagaccccaa ctttcttgtg tcttctctct   1320

tatcatcttc gctgtgatct ctctgtctcc ctctctctta tccaaaagat tagtataaaa   1380

ggatcgatct ttccttgtgg gttcttccat aaaacttcga ttctcgact               1429
```

<210> SEQ ID NO 2
<211> LENGTH: 500
<212> TYPE: DNA
<213> ORGANISM: Brassica napus

<400> SEQUENCE: 2

```
actttactct ttctctctaa tcgctcaata tacaaaagaa aagtgtttac atacacacat     60

catatatagt ttgcttttag tttccatgta accgaacggg tctgtttact tctatgaata    120

aaatagctag ttgatgattc tgttgattga tacactctat ggatagttca agattttatt    180

acaatccaac gatgatttgt atcaaataga gcccaccaga tcaagaaagc atactccaga    240

agcttttgtt caatctacca tcagataaca tatcaataac catcttcatg gtggaaccat    300

ctgcagcaaa cccacacctc ttcatttctt ctatgagttc aactgaagcg actacaccac    360

tacctccgag atgaactcgg atcagtgtgt tgtatgtaca ctcatttggc gcaatcccat    420

cctcctctcc catcttttta aacaacatat ccgcttcaga cagtgagcct ttcttacaca    480

gtcctgcaat cattatggta                                                500
```

<210> SEQ ID NO 3
<211> LENGTH: 2864
<212> TYPE: DNA
<213> ORGANISM: artificial sequence
<220> FEATURE:
<223> OTHER INFORMATION: yellow fluorescent protein gene expression cassette from pDAB113903

<400> SEQUENCE: 3

```
caacaaaaat gcactttttc gccaaaaata catttttctt caaaaaccgc aaaaatattt     60

tctgccaaac ccgtaaaaat actatttttc tgccgaaacg taaaaaaaaa tattttaatt    120

attttattaa caagtccact tggatgtaga tgaaaattta aaaaatgaaa agcaaacgaa    180

catagttgca ttcagatgat tcatctggat gcatggacga aatgaagaaa cgaacaacac    240

ccatatagag catctggata agacatctag atggatcatt acaaaagaac agggcctaaa    300

catgtgagat gtttgaagca atcagtcaaa agtaaccacc aaatcgaatt atgaaagcgt    360

tgattggatg gacaagttta acaaccattg tttgattgga caacgccgtt atctaaactt    420

ttagtgtgct gtgtacatca ttactatgaa tcagttagtt aaaaatatta tggtcagtga    480

atgacagtaa gattacttca gaacttgaga gatttaccgc aaaaagaaac acaataacgc    540

gtaggaaaaa tatcctctgt tttttgcaat tattctcgta gatttggtta tcagtaggta    600

tcacgtttta caaaaataga attacaatac atgccgcaag aaaaagactt tctcttttta    660

atttccccaa tttggttatc agtattcagt aagtttcaca tttttacaaa aatataaatt    720

aaaatacata ctgcaagaaa aatacttttt taatttcgcc aatttggtta tcagtagttt    780

tcacattttt acaaaaatat aattaaaata taaactgcaa caaaaagact tatcttttta    840

atttccccaa tttggttatc agtattcagt aggtttcaca tttacaaaaa tattattaaa    900

atacatactg caagaaacat acctttttaa tttcgccaat ctggttatca gtagttttca    960

catttttaca aaaatagaat taaaatacaa actgcaacaa aaagacttat ctttttaatt   1020

tccaccaata agttatttat ttatttaatc ctcccgtgag gaaaaagaca agattgagga   1080

tgaatatacg taactgaaaa ttgaggaaac agagccatca acctttcaac acggatgatc   1140

atcatcatca ctctctgccg cctttaaata gaaaccaaca aagacattct tgagcccaca   1200

ctcactcctt tcctatttct tcgctttgcg tgccttcctt ccttcttatc tacttgtatc   1260
```

```
ccacaaaaag ctacttaata ccatttaata aagaccccaa ctttcttgtg tcttctctct   1320

tatcatcttc gctgtgatct ctctgtctcc ctctctctta tccaaaagat tagtataaaa   1380

ggatcgatct ttccttgtgg gttcttccat aaaacttcga ttctcgactg gatctccatg   1440

tcatctggag cacttctctt tcatgggaag attccttacg ttgtggagat ggaagggaat   1500

gttgatggcc acacctttag catacgtggg aaaggctacg gagatgcctc agtgggaaag   1560

gtatgtttct gcttctacct ttgatatata tataataatt atcactaatt agtagtaata   1620

tagtatttca agtatttttt tcaaaataaa agaatgtagt atatagctat tgcttttctg   1680

tagtttataa gtgtgtatat tttaatttat aacttttcta atatatgacc aaaacatggt   1740

gatgtgcagg ttgatgcaca attcatctgt actaccggag atgttcctgt gccttggagc   1800

acacttgtca ccactctcac ctatggagca cagtgctttg ccaagtatgg tccagagttg   1860

aaggacttct acaagtcctg tatgccagat ggctatgtgc aagagcgcac aatcaccttt   1920

gaaggagatg gcaacttcaa gactagggct gaagtcacct ttgagaatgg gtctgtctac   1980

aatagggtca aactcaatgg tcaaggcttc aagaaagatg gtcacgtgtt gggaaagaac   2040

ttggagttca acttcactcc ccactgcctc tacatctggg gagaccaagc caaccacggt   2100

ctcaagtcag ccttcaagat atgtcatgag attactggca gcaaaggcga cttcatagtg   2160

gctgaccaca cccagatgaa cactcccatt ggtggaggtc cagttcatgt tccagagtat   2220

catcatatgt cttaccatgt gaaactttcc aaagatgtga cagaccacag agacaacatg   2280

agcttgaaag aaactgtcag agctgttgac tgtcgcaaga cctacctttg agtagttagc   2340

ttaatcacct agagctcggt caccacttta ctctttctct ctaatcgctc aatatacaaa   2400

agaaaagtgt ttacatacac acatcatata tagtttgctt ttagtttcca tgtaaccgaa   2460

cgggtctgtt tacttctatg aataaaatag ctagttgatg attctgttga ttgatacact   2520

ctatggatag ttcaagattt tattacaatc caacgatgat ttgtatcaaa tagagcccac   2580

cagatcaaga aagcatactc cagaagcttt tgttcaatct accatcagat aacatatcaa   2640

taaccatctt catggtggaa ccatctgcag caaacccaca cctcttcatt tcttctatga   2700

gttcaactga agcgactaca ccactacctc cgagatgaac tcggatcagt gtgttgtatg   2760

tacactcatt tggcgcaatc ccatcctcct ctcccatctt tttaaacaac atatccgctt   2820

cagacagtga gcctttctta cacagtcctg caatcattat ggta                   2864
```

<210> SEQ ID NO 4
<211> LENGTH: 1828
<212> TYPE: DNA
<213> ORGANISM: artificial sequence
<220> FEATURE:
<223> OTHER INFORMATION: phosphinothricin acetyl transferase gene expression cassette from pDAB113903

<400> SEQUENCE: 4

```
ccagaaggta attatccaag atgtagcatc aagaatccaa tgtttacggg aaaaactatg     60

gaagtattat gtaagctcag caagaagcag atcaatatgc ggcacatatg caacctatgt    120

tcaaaaatga agaatgtaca gatacaagat cctatactgc cagaatacga agaagaatac    180

gtagaaattg aaaaagaaga accaggcgaa gaaaagaatc ttgaagacgt aagcactgac    240

gacaacaatg aaaagaagaa gataaggtcg gtgattgtga aagagacata gaggacacat    300

gtaaggtgga aaatgtaagg gcggaaagta accttatcac aaaggaatct tatcccccac    360

tacttatcct tttatatttt tccgtgtcat ttttgccctt gagttttcct atataaggaa    420
```

ccaagttcgg catttgtgaa aacaagaaaa aatttggtgt aagctatttt ctttgaagta 480
ctgaggatac aacttcagag aaatttgtaa gtttgtaggt accagatctg gatcccaaac 540
catgtctccg gagaggagac cagttgagat taggccagct acagcagctg atatggccgc 600
ggtttgtgat atcgttaacc attacattga gacgtctaca gtgaacttta ggacagagcc 660
acaaacacca caagagtgga ttgatgatct agagaggttg caagatagat acccttggtt 720
ggttgctgag gttgagggtg ttgtggctgg tattgcttac gctgggccct ggaaggctag 780
gaacgcttac gattggacag ttgagagtac tgtttacgtg tcacataggc atcaaaggtt 840
gggcctagga tctacattgt acacacattt gcttaagtct atggaggcgc aaggttttaa 900
gtctgtggtt gctgttatag gccttccaaa cgatccatct gttaggttgc atgaggcttt 960
gggatacaca gcccggggta cattgcgcgc agctggatac aagcatggtg gatggcatga 1020
tgttggtttt tggcaaaggg attttgagtt gccagctcct ccaaggccag ttaggccagt 1080
tacccaaatc tgagtagtta gcttaatcac ctagagctcg atcggcggca atagcttctt 1140
agcgccatcc cgggttgatc ctatctgtgt tgaaatagtt gcggtgggca aggctctctt 1200
tcagaaagac aggcggccaa aggaacccaa ggtgaggtgg gctatggctc tcagttcctt 1260
gtggaagcgc ttggtctaag gtgcagaggt gttagcggga tgaagcaaaa gtgtccgatt 1320
gtaacaagat atgttgatcc tacgtaagga tattaaagta tgtattcatc actaatataa 1380
tcagtgtatt ccaatatgta ctacgatttc caatgtcttt attgtcgccg tatgtaatcg 1440
gcgtcacaaa ataatccccg gtgactttct tttaatccag gatgaaataa tatgttatta 1500
taatttttgc gatttggtcc gttataggaa ttgaagtgtg cttgaggtcg gtcgccacca 1560
ctcccatttc ataattttac atgtatttga aaaataaaaa tttatggtat tcaatttaaa 1620
cacgtatact tgtaaagaat gatatcttga aagaaatata gtttaaatat ttattgataa 1680
aataacaagt caggtattat agtccaagca aaaacataaa tttattgatg caagtttaaa 1740
ttcagaaata tttcaataac tgattatatc agctggtaca ttgccgtaga tgaaagactg 1800
agtgcgatat tatggtgtaa tacatagg 1828

<210> SEQ ID NO 5
<211> LENGTH: 2783
<212> TYPE: DNA
<213> ORGANISM: artificial sequence
<220> FEATURE:
<223> OTHER INFORMATION: yellow fluorescent protein gene expression cassette from pDAB9381

<400> SEQUENCE: 5
gtcgacctgc aggtcaacgg atcaggatat tcttgtttaa gatgttgaac tctatggagg 60
tttgtatgaa ctgatgatct aggaccggat aagttccctt cttcatagcg aacttattca 120
aagaatgttt tgtgtatcat tcttgttaca ttgttattaa tgaaaaaata ttattggtca 180
ttggactgaa cacgagtgtt aaatatggac caggccccaa ataagatcca ttgatatatg 240
aattaaataa caagaataaa tcgagtcacc aaaccacttg cctttttttaa cgagacttgt 300 tcaccaactt gatacaaaag tcattatcct atgcaaatca ataatcatac aaaaatatcc 360
aataacacta aaaaattaaa agaaatggat aatttcacaa tatgttatac gataaagaag 420
ttacttttcc aagaaattca ctgattttat aagcccactt gcattagata aatggcaaaa 480
aaaaacaaaa aggaaaagaa ataaagcacg aagaattcta gaaaatacga aatacgcttc 540
aatgcagtgg gacccacggt tcaattattg ccaattttca gctccaccgt atatttaaaa 600

```
aataaaacga taatgctaaa aaaatataaa tcgtaacgat cgttaaatct caacggctgg    660

atcttatgac gaccgttaga aattgtggtt gtcgacgagt cagtaataaa cggcgtcaaa    720

gtggttgcag ccggcacaca cgagtcgtgt ttatcaactc aaagcacaaa tacttttcct    780

caacctaaaa ataaggcaat tagccaaaaa caactttgcg tgtaaacaac gctcaataca    840

cgtgtcattt tattattagc tattgcttca ccgccttagc tttctcgtga cctagtcgtc    900

ctcgtctttt cttcttcttc ttctataaaa caatacccaa agcttcttct tcacaattca    960

gatttcaatt tctcaaaatc ttaaaaactt tctctcaatt ctctctaccg tgatcaaggt   1020

aaatttctgt gttccttatt ctctcaaaat cttcgatttt gttttcgttc gatcccaatt   1080

tcgtatatgt tctttggttt agattctgtt aatcttagat cgaagacgat tttctgggtt   1140

tgatcgttag atatcatctt aattctcgat tagggtttca taaatatcat ccgatttgtt   1200

caaataattt gagttttgtc gaataattac tcttcgattt gtgatttcta tctagatctg   1260

gtgttagttt ctagtttgtg cgatcgaatt tgtcgattaa tctgagtttt tctgattaac   1320

agagatctcc atgtcatctg gagcacttct ctttcatggg aagattcctt acgttgtgga   1380

gatggaaggg aatgttgatg gccacacctt tagcatacgt gggaaaggct acggagatgc   1440

ctcagtggga aaggtatgtt tctgcttcta cctttgatat atatataata attatcacta   1500

attagtagta atatagtatt tcaagtattt ttttcaaaat aaaagaatgt agtatatagc   1560

tattgctttt ctgtagttta taagtgtgta tattttaatt tataactttt ctaatatatg   1620

accaaaacat ggtgatgtgc aggttgatgc acaattcatc tgtactaccg gagatgttcc   1680

tgtgccttgg agcacacttg tcaccactct cacctatgga gcacagtgct ttgccaagta   1740

tggtccagag ttgaaggact tctacaagtc ctgtatgcca gatggctatg tgcaagagcg   1800

cacaatcacc tttgaaggag atggcaactt caagactagg gctgaagtca cctttgagaa   1860

tgggtctgtc tacaataggg tcaaactcaa tggtcaaggc ttcaagaaag atggtcacgt   1920

gttgggaaag aacttggagt tcaacttcac tccccactgc ctctacatct ggggagacca   1980

agccaaccac ggtctcaagt cagccttcaa gatatgtcat gagattactg gcagcaaagg   2040

cgacttcata gtggctgacc acacccagat gaacactccc attggtggag gtccagttca   2100

tgttccagag tatcatcata tgtcttacca tgtgaaactt tccaaagatg tgacagacca   2160

cagagacaac atgagcttga aagaaactgt cagagctgtt gactgtcgca agacctacct   2220

ttgagtagtt agcttaatca cctagagctc ggtcaccagc ataattttta ttaatgtact   2280

aaattactgt tttgttaaat gcaattttgc tttctcggga ttttaatatc aaaatctatt   2340

tagaaataca caatattttg ttgcaggctt gctggagaat cgatctgcta tcataaaaat   2400

tacaaaaaaa ttttatttgc ctcaattatt ttaggattgg tattaaggac gcttaaatta   2460

tttgtcgggt cactacgcat cattgtgatt gagaagatca gcgatacgaa atattcgtag   2520

tactatcgat aatttatttg aaaattcata agaaaagcaa acgttacatg aattgatgaa   2580

acaatacaaa gacagataaa gccacgcaca tttaggatat tggccgagat tactgaatat   2640

tgagtaagat cacggaattt ctgacaggag catgtcttca attcagccca aatggcagtt   2700

gaaatactca aaccgcccca tatgcaggag cggatcattc attgtttgtt tggttgcctt   2760

tgccaacatg ggagtccaag gtt                                          2783
```

<210> SEQ ID NO 6
<211> LENGTH: 1828
<212> TYPE: DNA

<213> ORGANISM: Artificial Sequence
<220> FEATURE:
<223> OTHER INFORMATION: phosphinothricin acetyl transferase gene expression cassette from pDAB9381

<400> SEQUENCE: 6

```
ccagaaggta attatccaag atgtagcatc aagaatccaa tgtttacggg aaaaactatg     60
gaagtattat gtaagctcag caagaagcag atcaatatgc ggcacatatg caacctatgt    120
tcaaaaatga agaatgtaca gatacaagat cctatactgc cagaatacga agaagaatac    180
gtagaaattg aaaaagaaga accaggcgaa gaaaagaatc ttgaagacgt aagcactgac    240
gacaacaatg aaaagaagaa gataaggtcg gtgattgtga aagagacata gaggacacat    300
gtaaggtgga aaatgtaagg gcggaaagta accttatcac aaaggaatct tatcccccac    360
tacttatcct tttatatttt tccgtgtcat ttttgccctt gagttttcct atataaggaa    420
ccaagttcgg catttgtgaa aacaagaaaa aatttggtgt aagctatttt ctttgaagta    480
ctgaggatac aacttcagag aaatttgtaa gtttgtaggt accagatctg gatcccaaac    540
catgtctccg gagaggagac cagttgagat taggccagct acagcagctg atatggccgc    600
ggtttgtgat atcgttaacc attacattga gacgtctaca gtgaacttta ggacagagcc    660
acaaacacca caagagtgga ttgatgatct agagaggttg caagatagat acccttggtt    720
ggttgctgag gttgagggtg ttgtggctgg tattgcttac gctgggccct ggaaggctag    780
gaacgcttac gattggacag ttgagagtac tgtttacgtg tcacataggc atcaaaggtt    840
gggcctagga tctacattgt acacacattt gcttaagtct atggaggcgc aaggttttaa    900
gtctgtggtt gctgttatag gccttccaaa cgatccatct gttaggttgc atgaggcttt    960
gggatacaca gcccggggta cattgcgcgc agctggatac aagcatggtg gatggcatga   1020
tgttggtttt tggcaaaggg attttgagtt gccagctcct ccaaggccag ttaggccagt   1080
tacccaaatc tgagtagtta gcttaatcac ctagagctcg atcggcggca atagcttctt   1140
agcgccatcc cgggttgatc ctatctgtgt tgaaatagtt gcggtgggca aggctctctt   1200
tcagaaagac aggcggccaa aggaacccaa ggtgaggtgg gctatggctc tcagttcctt   1260
gtggaagcgc ttggtctaag gtgcagaggt gttagcggga tgaagcaaaa gtgtccgatt   1320
gtaacaagat atgttgatcc tacgtaagga tattaaagta tgtattcatc actaatataa   1380
tcagtgtatt ccaatatgta ctacgatttc caatgtcttt attgtcgccg tatgtaatcg   1440
gcgtcacaaa ataatccccg gtgactttct tttaatccag gatgaaataa tatgttatta   1500
taatttttgc gatttggtcc gttataggaa ttgaagtgtg cttgaggtcg gtcgccacca   1560
ctcccatttc ataattttac atgtatttga aaaataaaaa tttatggtat tcaatttaaa   1620
cacgtatact tgtaaagaat gatatcttga aagaaatata gtttaaatat ttattgataa   1680
aataacaagt caggtattat agtccaagca aaaacataaa tttattgatg caagtttaaa   1740
ttcagaaata tttcaataac tgattatatc agctggtaca ttgccgtaga tgaaagactg   1800
agtgcgatat tatggtgtaa tacatagg                                      1828
```

<210> SEQ ID NO 7
<211> LENGTH: 29
<212> TYPE: DNA
<213> ORGANISM: artificial sequence
<220> FEATURE:
<223> OTHER INFORMATION: oligonucleotide primer

<400> SEQUENCE: 7

-continued

```
acaagagtgg attgatgatc tagagaggt                                    29


<210> SEQ ID NO 8
<211> LENGTH: 29
<212> TYPE: DNA
<213> ORGANISM: artificial sequence
<220> FEATURE:
<223> OTHER INFORMATION: oligonucleotide primer

<400> SEQUENCE: 8

ctttgatgcc tatgtgacac gtaaacagt                                    29


<210> SEQ ID NO 9
<211> LENGTH: 29
<212> TYPE: DNA
<213> ORGANISM: artificial sequence
<220> FEATURE:
<223> OTHER INFORMATION: oligonucleotide probe

<400> SEQUENCE: 9

agggtgttgt ggctggtatt gcttacgct                                    29


<210> SEQ ID NO 10
<211> LENGTH: 22
<212> TYPE: DNA
<213> ORGANISM: artificial sequence
<220> FEATURE:
<223> OTHER INFORMATION: oligonucleotide primer

<400> SEQUENCE: 10

gaggattagg gtttcaacgg ag                                           22


<210> SEQ ID NO 11
<211> LENGTH: 21
<212> TYPE: DNA
<213> ORGANISM: artificial sequence
<220> FEATURE:
<223> OTHER INFORMATION: oligonucleotide primer

<400> SEQUENCE: 11

gagaattgag ctgagacgag g                                            21


<210> SEQ ID NO 12
<211> LENGTH: 25
<212> TYPE: DNA
<213> ORGANISM: artificial sequence
<220> FEATURE:
<223> OTHER INFORMATION: oligonucleotide probe

<400> SEQUENCE: 12

agagaagttt cgacggattt cgggc                                        25
```

*BRASSICA NAPUS* SEED SPECIFIC PROMOTERS IDENTIFIED BY MICROARRAY ANALYSIS

CROSS-REFERENCE TO RELATED APPLICATIONS

This is a national phase entry under 35 U.S.C. § 371 of international Patent Application PCT/US2015/067584, filed Dec. 28, 2015, published in English as International Patent Publication No. WO2016111859 on Jul. 14, 2016, which claims priority to U.S. Patent Application No. 62/100,389 filed on Jan. 6, 2015, all of which are incorporated in their entirety by reference herein.

TECHNICAL FIELD

This invention is generally related to the field of plant molecular biology, and more specifically, to the field of expression of transgenes in plants.

BACKGROUND

Many plant species are capable of being transformed with transgenes to introduce agronomically desirable traits or characteristics. The resulting transgenic plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation of the plant genome results in transgenic plants that possess desirable traits and phenotypes. However, mechanisms that allow the production of transgenic plant species to highly express multiple transgenes engineered as a trait stack are desirable.

Likewise, mechanisms that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Furthermore, it may be desirable to express a transgene in leaf and stem tissues of a plant.

Described herein are *Brassica napus* GALE1 gene promoter regulatory elements, constructs/vectors containing the *Brassica napus* GALE1 gene promoter regulatory, and methods utilizing *Brassica napus* GALE1 gene promoter regulatory elements.

DISCLOSURE

Disclosed herein are sequences, constructs, and methods for expressing a transgene in plant cells and/or plant tissues.

In an embodiment the disclosure relates to a gene expression cassette comprising a promoter operably linked to a transgene, wherein the promoter comprises a polynucleotide that hybridizes under stringent conditions to a polynucleotide probe comprising a sequence identity of at least 90% to a complement of SEQ ID NO:1. In further embodiments, the promoter comprises a polynucleotide that has at least 90% sequence identity to SEQ ID NO:1. In additional embodiments, the promoter comprises a polynucleotide comprising an intron. In other embodiments, the intron has at least 90% sequence identity to a rice actin intron, a maize ubiquitin intron, or an *Arabadiopsis thaliana* ubiquitin 10 intron. In an embodiment the promoter comprises a polynucleotide comprising a 5'-untranslated region. In other embodiments, the operably linked transgene encodes a polypeptide or a small RNA. In a subsequent embodiment, the transgene is selected from the group consisting of insecticidal resistance transgene, herbicide tolerance transgene, nitrogen use efficiency transgene, water use efficiency transgene, nutritional quality transgene, DNA binding transgene, and selectable marker transgene. In yet another embodiment, the gene expression cassette further comprises a 3'-untranslated region. In an embodiment the 3'-untranslated region comprises a polynucleotide that has a sequence identity of at least 90% to SEQ ID NO:2. In an embodiment, a recombinant vector comprises the gene expression cassette. In a further aspect of the embodiment, the recombinant vector is selected from the group consisting of a plasmid, a cosmid, a bacterial artificial chromosome, a virus, and a bacteriophage. In an embodiment, a transgenic cell comprises the gene expression cassette. In a subsequent aspect of the embodiment, the cell is a transgenic plant cell. In an embodiment, a transgenic plant comprises the transgenic plant cell. In a further aspect of the embodiment, the transgenic plant is a monocotyledonous plant or dicotyledonous plant. In other aspects of the embodiment, the dicotyledonous plant is selected from the group consisting of an *Arabidopsis* plant, a tobacco plant, a soybean plant, a canola plant and a cotton plant. In an embodiment, a transgenic seed is obtained from the transgenic plant. In a subsequent embodiment, the promoter is a tissue-preferred promoter. In an additional embodiment, the tissue-preferred promoter is an ovule or seed tissue-preferred promoter. In an embodiment, the seed tissue-preferred promoter is an endosperm tissue-preferred promoter. In yet another embodiment, the promoter comprises a polynucleotide sequence of nucleotides 1-1429 of SEQ ID NO:1.

In an embodiment the disclosure relates to a transgenic cell comprising a synthetic polynucleotide that hybridizes under stringent conditions to a polynucleotide probe comprising a sequence identity of at least 90% to a complement of SEQ ID NO:1. In an additional embodiment, the synthetic polynucleotide has at least 90% sequence identity to SEQ ID NO:1. In additional embodiments, the synthetic polynucleotide comprises a polynucleotide comprising an intron. In other embodiments, the intron has a sequence identity of at least 90% to a rice actin intron, a maize ubiquitin intron, or an *Arabadiopsis thaliana* ubiquitin 10 intron. In an embodiment, the synthetic polynucleotide comprises a 5'-untranslated region. In a further embodiment, the transgenic cell is a transgenic plant cell. In a subsequent embodiment, the transgenic plant cell is produced by a plant transformation method. In an additional embodiment, the plant transformation method is selected from the group consisting of an *Agrobacterium*-mediated transformation method, a biolistics transformation method, a silicon carbide transformation method, a protoplast transformation method, and a liposome transformation method. In an embodiment, a transgenic plant comprises the transgenic plant cell. In a further embodiment, the transgenic plant is a monocotyledonous plant or dicotyledonous plant. In other embodiments, the monocotyledonous plant is selected from the group consisting of a maize plant, a rice plant, and a wheat plant. In other aspects of the embodiment, the dicotyledonous plant is selected from the group consisting of an *Arabidopsis* plant, a tobacco plant, a soybean plant, a canola plant and a cotton plant. In an embodiment, a transgenic seed is obtained from the transgenic plant. In an additional embodiment, the promoter is a tissue-preferred promoter. In an additional embodiment, the tissue-preferred promoter is an ovule or seed tissue-preferred promoter. In an embodiment, the seed tissue-preferred promoter is an endosperm tissue-preferred promoter. In another embodiment, the synthetic polynucleotide comprises a polynucleotide sequence of nucleotides 1-1429 of SEQ ID NO:1.

In an embodiment the disclosure relates to a purified polynucleotide promoter, wherein the promoter comprises a polynucleotide that hybridizes under stringent conditions to a polynucleotide probe comprising a sequence identity of at least 90% to a complement of SEQ ID NO:1. In further embodiments, the purified polynucleotide promoter has at least 90% sequence identity to SEQ ID NO:1. In additional embodiments, the purified polynucleotide promoter comprises a polynucleotide comprising an intron. In other embodiments, the intron has at least 90% identity to a rice actin intron, a maize ubiquitin intron, or an *Arabadiopsis thaliana* ubiquitin 10 intron. In an embodiment, the purified polynucleotide promoter comprises a 5'-untranslated region. In another embodiment, the purified polynucleotide is operably linked to a transgene. In a subsequent embodiment, the operably linked transgene encodes a polypeptide or is a small RNA. In an embodiment, a gene expression cassette comprises the purified polynucleotide sequence operably linked to the transgene, which is operably linked to a 3'-untranslated region. In an embodiment the 3'-untranslated region comprises a polynucleotide that has a sequence identity of at least 90% to SEQ ID NO:2. In another embodiment, the transgene is selected from the group consisting of insecticidal resistance transgene, herbicide tolerance transgene, nitrogen use efficiency transgene, water use efficiency transgene, nutritional quality transgene, DNA binding transgene, and selectable marker transgene. In an embodiment, a recombinant vector comprises the gene expression cassette. In an additional embodiment, the recombinant vector is selected from the group consisting of a plasmid vector, a cosmid vector, and a BAC vector. In an embodiment, a transgenic cell comprises the gene expression cassette. In a subsequent embodiment the transgenic cell is a transgenic plant cell. In an embodiment, a transgenic plant comprises the transgenic plant cell. In an additional embodiment, the transgenic plant is a monocotyledonous or dicotyledonous plant. In yet a further embodiment, the monocotyledonous plant is selected from the group consisting of a maize plant, a wheat plant, and a rice plant. In other aspects of the embodiment, the dicotyledonous plant is selected from the group consisting of an *Arabidopsis* plant, a tobacco plant, a soybean plant, a canola plant and a cotton plant. In an embodiment, a transgenic seed is obtained from the transgenic plant. In a subsequent embodiment, the purified polynucleotide sequence promotes tissue-preferred expression of a transgene. In an additional embodiment, the tissue-preferred promoter is an ovule or seed tissue-preferred promoter. In an embodiment, the seed tissue-preferred promoter is an endosperm tissue-preferred promoter. In other embodiments, the purified polynucleotide comprises a polynucleotide sequence of nucleotides 1-1429 of SEQ ID NO:1.

In an embodiment the disclosure relates to a method for expressing a heterologous coding sequence in a transgenic plant, the method comprising:

a) transforming a plant cell with a gene expression cassette comprising a polynucleotide sequence comprising a sequence identity of at least 90% to SEQ ID NO:1 operably linked to the heterologous coding sequence, which is operably linked to a 3'-untranslated region;
b) isolating the transformed plant cell comprising the gene expression cassette;
c) regenerating the transformed plant cell into a transgenic plant; and,
d) obtaining the transgenic plant, wherein the transgenic plant comprises the gene expression cassette comprising the polynucleotide sequence comprising SEQ ID NO:1.

In additional embodiments, the polynucleotide sequence comprises an intron. In other embodiments, the intron has a sequence identity of at least 90% to a rice actin intron, a maize ubiquitin intron, or an *Arabadiopsis thaliana* ubiquitin 10 intron. In an embodiment, the polynucleotide sequence has at least 90% sequence identity to SEQ ID NO:1. In a further embodiment, the heterologous coding sequence is selected from the group consisting of insecticidal resistance coding sequences, herbicide tolerance coding sequences, nitrogen use efficiency coding sequences, water use efficiency coding sequences, nutritional quality coding sequences, DNA binding coding sequences, and selectable marker coding sequences. In an additional embodiment, transforming of a plant cell utilizes a plant transformation method. In yet another embodiment, the plant transformation method is selected from the group consisting of an *Agrobacterium*-mediated transformation method, a biolistics transformation method, a silicon carbide transformation method, a protoplast transformation method, and a liposome transformation method. In other embodiments, the transgenic plant is a monocotyledonous transgenic plant or a dicotyledonous transgenic plant. In further embodiments, the monocotyledonous transgenic plant is selected from the group consisting of a maize plant, a wheat plant, and a rice plant. In an embodiment, a transgenic seed is obtained from the transgenic plant. In other aspects of the embodiment, the dicotyledonous plant is selected from the group consisting of an *Arabidopsis* plant, a tobacco plant, a soybean plant, a canola plant and a cotton plant. In a further embodiment, the heterologous coding sequence is preferentially expressed in a tissue. In an additional embodiment, the tissue-preferred promoter is an ovule or seed tissue-preferred promoter. In an embodiment, the seed tissue-preferred promoter is an endosperm tissue-preferred promoter. In other embodiments, the polynucleotide comprises a sequence of nucleotides 1-1429 of SEQ ID NO:1.

In an embodiment the disclosure relates to a method for isolating a polynucleotide sequence comprising a sequence identity of at least 90% to SEQ ID NO:1, the method comprising:

a) identifying the polynucleotide sequence comprising a sequence identity of at least 90% to SEQ ID NO:1;
b) producing a plurality of oligonucleotide primer sequences, wherein the oligonucleotide primer sequences bind to the polynucleotide sequence comprising a sequence identity of at least 90% to SEQ ID NO:1;

c) amplifying the polynucleotide sequence comprising a sequence identity of at least 90% to SEQ ID NO:1 from a DNA sample with oligonucleotide primer sequences selected from the plurality of oligonucleotide primer sequences; and, d) isolating the polynucleotide sequence comprising a sequence identity of at least 90% to SEQ ID NO:1.

In additional embodiments, the polynucleotide sequence comprises an intron. In other embodiments, the intron has a sequence identity of at least 90% to a rice actin intron, a maize ubiquitin intron, or an *Arabadiopsis thaliana* ubiquitin 10 intron. In an embodiment, the polynucleotide sequence comprise a 5'-untranslated region. In an additional embodiment, the isolated polynucleotide sequence comprising a sequence identity of at least 90% to SEQ ID NO:1 is operably linked to a transgene. In a further embodiment, the operably linked transgene encodes a polypeptide. In an embodiment, a gene expression cassette comprises a polynucleotide sequence with at least 90% sequence identity to SEQ ID NO:1 operably linked to a transgene, wherein the transgene is operably linked to a 3'-untranslated region. In an embodiment the 3'-untranslated region comprises a polynucleotide that has a sequence identity of at least 90% to SEQ ID NO:2. In a further embodiment, the transgene is selected from the group consisting of insecticidal resistance coding sequences, herbicide tolerance coding sequences, nitrogen use efficiency coding sequences, water use efficiency coding sequences, nutritional quality coding sequences, DNA binding coding sequences, and selectable marker coding sequences. In an embodiment, a recombinant vector comprises the gene expression cassette. In a further embodiment, the vector is selected from the group consisting of a plasmid vector, a cosmid vector, and a BAC vector. In an embodiment, a transgenic cell comprises the gene expression cassette. In an additional embodiment, the transgenic cell is a transgenic plant cell. In an embodiment, a transgenic plant comprises the transgenic plant cell. In an additional embodiment, the transgenic plant is a monocotyledonous plant or a dicotyledonous plant. In a further embodiment, the monocotyledonous plant is selected from the group consisting of a maize plant, a wheat plant, and a rice plant. In an embodiment, a transgenic seed is obtained from the transgenic plant. In other aspects of the embodiment, the dicotyledonous plant is selected from the group consisting of an *Arabidopsis* plant, a tobacco plant, a soybean plant, a canola plant and a cotton plant. In other embodiments, the isolated polynucleotide comprises a polynucleotide sequence of nucleotides 1-1429 of SEQ ID NO:1.

In an embodiment the disclosure relates to a method for manufacturing a synthetic polynucleotide sequence comprising a sequence identity of at least 90% to SEQ ID NO:1, the method comprising:

a) identifying the polynucleotide sequence comprising SEQ ID NO:1;

b) isolating the polynucleotide sequence comprising SEQ ID NO:1;

c) defining a plurality of polynucleotide sequences that comprise a sequence identity of at least 90% to SEQ ID NO:1;

d) synthesizing a polynucleotide sequence comprising a sequence identity of at least 90% to SEQ ID NO:1; and, e) manufacturing a synthetic polynucleotide sequence comprising a sequence identity of at least 90% to SEQ ID NO:1.

In a further embodiment, the synthesizing comprises:

a) identifying the polynucleotide sequence comprising a sequence identity of at least 90% to SEQ ID NO:1;

b) producing a plurality of oligonucleotide primer sequences, wherein the oligonucleotide primer sequences bind to the polynucleotide sequence comprising a sequence identity of at least 90% to SEQ ID NO:1;

c) ligating the plurality of oligonucleotide primer sequences to synthesize the polynucleotide sequence comprising a sequence identity of at least 90% to SEQ ID NO:1.

In additional embodiments, the synthesized polynucleotide sequence comprises an intron. In other embodiments, the intron has a sequence identity of at least 90% to a rice actin intron, a maize ubiquitin intron, or an *Arabadiopsis thaliana* ubiquitin 10 intron. In an embodiment, the synthesized polynucleotide sequence comprises a 5'-untranslated region. In an additional embodiment, the synthesized polynucleotide sequence comprises a sequence identity of at least 90% to SEQ ID NO:1 that is operably linked to a transgene. In yet another embodiment, the operably linked transgene encodes a polypeptide. In an embodiment, a gene expression cassette comprises the synthesized polynucleotide sequence comprising a sequence identity of at least 90% to SEQ ID NO:1 operably linked to the transgene, that is operably linked to a 3'-untranslated region. In an embodiment the 3'-untranslated region comprises a polynucleotide that has a sequence identity of at least 90% to SEQ ID NO:2. In yet another embodiment, the transgene is selected from the group consisting of insecticidal resistance transgene, herbicide tolerance transgene, nitrogen use efficiency transgene, water use efficiency transgene, nutritional quality transgene, DNA binding transgene, and selectable marker transgene. In an embodiment, a recombinant vector comprises the gene expression cassette. In an additional embodiment, the recombinant vector is selected from the group consisting of a plasmid vector, a cosmid vector, and a BAC vector. In an embodiment, a transgenic cell comprises the gene expression cassette. In a further embodiment, the transgenic cell is a transgenic plant cell. In an embodiment, a transgenic plant comprises the transgenic plant cell. In a further embodiment, the transgenic plant is a monocotyledonous or dicotyledonous plant. In other embodiments, the monocotyledonous plant is selected from the group consisting of a maize plant, a wheat plant and a rice plant. In other aspects of the embodiment, the dicotyledonous plant is selected from the group consisting of an *Arabidopsis* plant, a tobacco plant, a soybean plant, a canola plant and a cotton plant. In an embodiment, a transgenic seed is obtained from the transgenic plant. In other embodiments, the synthetic polynucleotide comprises a polynucleotide sequence of nucleotides 1-1429 of SEQ ID NO:1.

In an embodiment, a construct includes a gene expression cassette comprising a *Brassica napus* GALE1 gene promoter of SEQ ID NO:1. In an embodiment, a gene expression cassette includes a *Brassica napus* GALE1 gene promoter of SEQ ID NO:1 operably linked to a transgene or a heterologous coding sequence. In an embodiment, a gene expression cassette includes a *Brassica napus* GALE1 gene 3'-UTR of SEQ ID NO:2 operably linked to a transgene. In an embodiment, a gene expression cassette includes a *Brassica napus* GALE1 gene 3'-UTR of SEQ ID NO:2 operably linked to a promoter. In a further embodiment, a gene expression cassette includes a *Brassica napus* GALE1 gene 3'-UTR of SEQ ID NO:2 operably linked to a *Brassica napus* GALE1 gene promoter of SEQ ID NO:1. In an embodiment, a gene expression cassette includes a *Brassica napus* GALE1 gene promoter of SEQ ID NO:1 operably linked to a transgene or a heterologous coding sequence. In an embodiment, a gene expression cassette includes at least one, two, three, four, five, six, seven, eight, nine, ten, or more transgenes.

In an embodiment, a gene expression cassette includes independently a) a *Brassica napus* GALE1 gene promoter of SEQ ID NO:1, and b) a *Brassica napus* GALE1 gene 3'-UTR of SEQ ID NO:2.

Methods of growing plants expressing a transgene using *Brassica napus* GALE1 gene promoters of SEQ ID NO:1, and 3'-UTRs of SEQ ID NO:2 are disclosed herein. Methods of culturing plant tissues and cells expressing a transgene using the *Brassica napus* GALE1 gene promoters of SEQ ID NO:1, and 3'-UTRs of SEQ ID NO:2 are also disclosed herein. In an embodiment, methods, as disclosed herein, include tissue-specific gene expression in plant leaves and stems.

In an embodiment, a gene expression cassette includes a promoter polynucleotide sequence of SEQ ID NO:1 that was obtained from the *Brassica napus* GALE1 gene.

MODE(S) FOR CARRYING OUT THE INVENTION

Definitions

Figure 1:
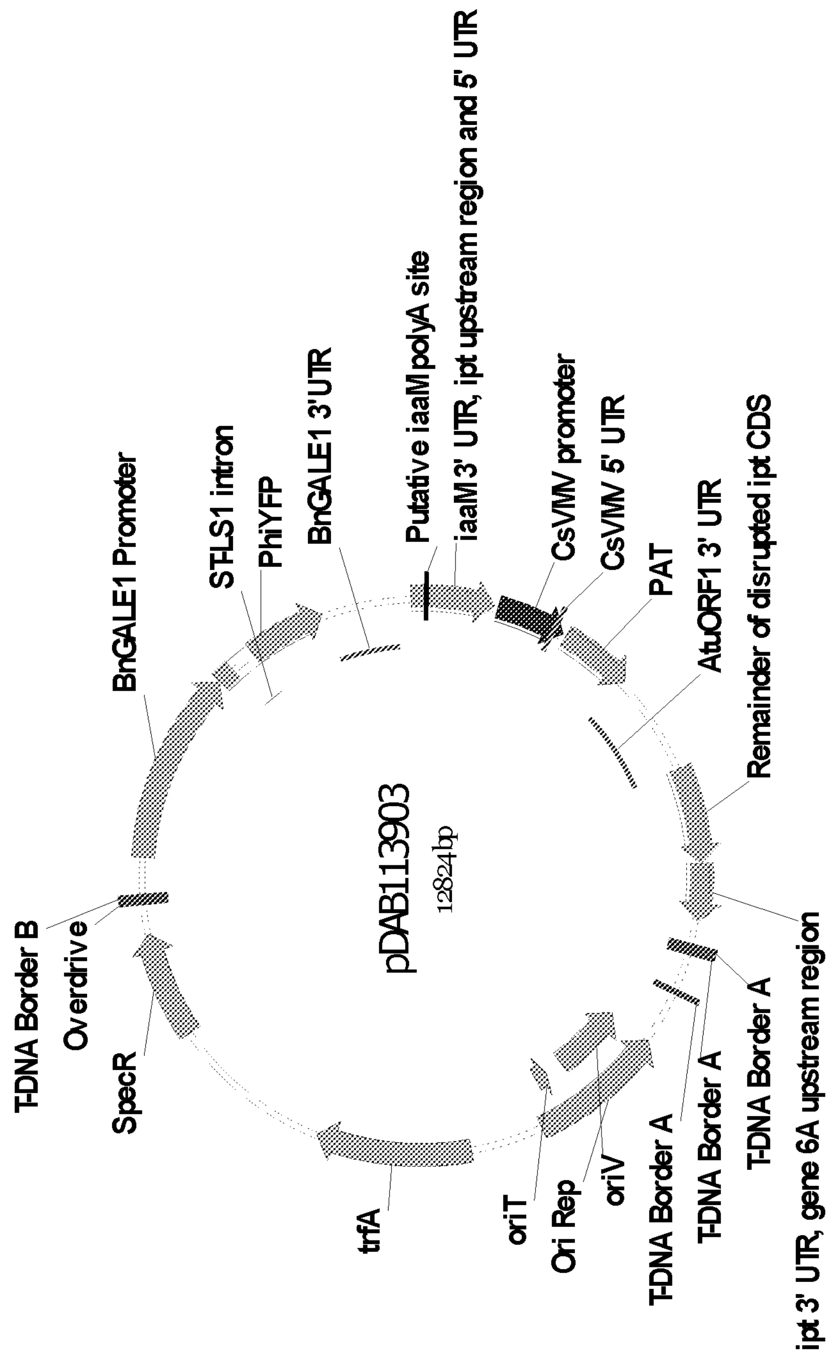
FIG. 1 shows a plasmid map of pDAB113903.

As used herein, the articles, "a," "an," and "the" include plural references unless the context clearly and unambiguously dictates otherwise.

As used herein, the term "backcrossing" refers to a process in which a breeder crosses hybrid progeny back to one of the parents, for example, a first generation hybrid F1 with one of the parental genotypes of the F1 hybrid.

As used herein, the term "intron" refers to any nucleic acid sequence comprised in a gene (or expressed nucleotide sequence of interest) that is transcribed but not translated. Introns include untranslated nucleic acid sequence within an expressed sequence of DNA, as well as corresponding sequence in RNA molecules transcribed therefrom.

A construct described herein can also contain sequences that enhance translation and/or mRNA stability such as introns. An example of one such intron is the first intron of gene II of the histone variant of *Arabidopsis thaliana* or any other commonly known intron sequence. Introns can be used in combination with a promoter sequence to enhance translation and/or mRNA stability.

As used herein, the terms "5' untranslated region" or "5'-UTR" refer to an untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "3' untranslated region" or "3'-UTR" refers to an untranslated segment in a 3' terminus of the pre-mRNAs or mature mRNAs. For example, on mature mRNAs this region harbors the poly-(A) tail and is known to have many roles in mRNA stability, translation initiation, and mRNA export.

As used herein, the term "polyadenylation signal" refers to a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) *Plant Physiology* 138(3); 1457-1468.

As used herein, the term "isolated" refers to a biological component (including a nucleic acid or protein) that has been separated from other biological components in the cell of the organism in which the component naturally occurs (i.e., other chromosomal and extra-chromosomal DNA).

As used herein, the term "purified" in reference to nucleic acid molecules does not require absolute purity (such as a homogeneous preparation); instead, it represents an indication that the sequence is relatively more pure than in its native cellular environment (compared to the natural level this level should be at least 2-5 fold greater, e.g., in terms of concentration or gene expression levels). The DNA molecules may be obtained directly from total genomic DNA or from total genomic RNA. In addition, cDNA clones are not naturally occurring, but rather are preferably obtained via manipulation of a partially purified, naturally occurring substance (messenger RNA that is reverse transcribed by a reverse transcriptase polymerase). The construction of a cDNA library from mRNA involves the creation of a synthetic substance (cDNA). Individual cDNA clones can be purified from the synthetic library by clonal selection of the cells carrying the cDNA library. Thus, the process which includes the construction of a cDNA library from mRNA and purification of distinct cDNA clones yields an approximately $10^6$-fold purification of the native message. Likewise, a promoter DNA sequence could be cloned into a plasmid. Such a clone is not naturally occurring, but rather is preferably obtained via manipulation of a partially purified, naturally occurring substance such as a genomic DNA library or directly from genomic DNA. Thus, purification of at least one order of magnitude, preferably two or three orders, and more preferably four or five orders of magnitude is favored in these techniques.

Similarly, purification represents an indication that a chemical or functional change in the component DNA sequence has occurred. Nucleic acid molecules and proteins that have been "purified" include nucleic acid molecules and proteins purified by standard purification methods. The term "purified" also embraces nucleic acids and proteins prepared by recombinant DNA methods in a host cell (e.g., plant cells), as well as chemically-synthesized nucleic acid molecules, proteins, and peptides.

The term "recombinant" refers to a cell or organism in which genetic recombination has occurred. It also includes a molecule (e.g., a vector, plasmid, nucleic acid, polypeptide, or a small RNA) that has been artificially or synthetically (i.e., non-naturally) altered by human intervention. The alteration can be performed on the molecule within, or removed from, its natural environment or state.

As used herein, the term "expression" refers to the process by which a polynucleotide is transcribed into mRNA (including small RNA molecules) and/or the process by which the transcribed mRNA (also referred to as "transcript") is subsequently translated into peptides, polypeptides, or proteins. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, the terms "homology-based gene silencing" or "HBGS" are generic tams that include both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. Involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. A single transgene locus can be described to trigger both TGS and PTGS, owing to the production of dsRNA corresponding to promoter and transcribed sequences of different target genes.

As used herein, the terms "nucleic acid molecule," "nucleic acid," or "polynucleotide" (all three terms are synonymous with one another) refer to a polymeric form of nucleotides, which may include both sense and anti-sense strands of RNA, cDNA, genomic DNA, and synthetic forms, and mixed polymers thereof. "A nucleotide" may refer to a ribonucleotide, deoxyribonucleotide, or a modified form of either type of nucleotide. A nucleic acid molecule is usually at least 10 bases in length, unless otherwise specified. The terms may refer to a molecule of RNA or DNA of indeterminate length. The terms include single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This indicates that RNA is made by sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the term "base position" refers to the location of a given base or nucleotide residue within a designated nucleic acid. A designated nucleic acid may be defined by alignment with a reference nucleic acid.

As used herein, the term "hybridization" refers to a process where oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and bonding of a pyrimidine to a purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the terms "specifically hybridizable" and "specifically complementary" refers to a sufficient degree of complementarity such that stable and specific binding occurs between an oligonucleotide and the DNA or RNA target. Oligonucleotides need not be 100% complementary to the target sequence to specifically hybridize. An oligonucleotide is specifically hybridizable when binding of the oligonucleotide to the target DNA or RNA molecule interferes with the normal function of the target DNA or RNA, and there is sufficient degree of complementarity to avoid non-specific binding of an oligonucleotide to non-target sequences under conditions where specific binding is desired, for example, under physiological conditions in the case of in vivo assays or systems. Such binding is referred to as specific hybridization. Hybridization conditions resulting in particular degrees of stringency will vary depending upon the nature of the chosen hybridization method and the composition and length of the hybridizing nucleic acid sequences. Generally, the temperature of hybridization and the ionic strength (especially $Na^+$ and/or $Mg^{2+}$ concentration) of a hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989.

As used herein, the term "stringent conditions" encompasses conditions under which hybridization will only occur if there is less than 50% mismatch between the hybridization molecule and the DNA target. "Stringent conditions"

include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes. The following are representative, non-limiting hybridization conditions:

Very High Stringency: hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2-3×SSC buffer at room temperature to 55° C. for 20-30 minutes each.

In an embodiment, specifically hybridizable nucleic acid molecules can remain bound under very high stringency hybridization conditions. In an embodiment, specifically hybridizable nucleic acid molecules can remain bound under high stringency hybridization conditions. In an embodiment, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in polymerase chain reaction, a technique for the amplification of small DNA sequences. In polymerase chain reaction, an oligonucleotide is typically referred to as a "primer" which allows a DNA polymerase to extend the oligonucleotide and replicate the complementary strand.

As used herein, the terms "Polymerase Chain Reaction" or "PCR" refer to a procedure or technique in which minute amounts of nucleic acid, RNA and/or DNA, are amplified as described in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51:263 (1987); Erlich, ed., PCR Technology, (Stockton Press, NY, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer that may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide or polynucleotide sequence that hybridizes to a target sequence. In the TAQMAN® or TAQMAN®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides.

In the Southern blot assay procedure, the probe hybridizes to a DNA fragment that is attached to a membrane. A probe includes about ten nucleotides, about 100 nucleotides, about 250 nucleotides, about 500 nucleotides, about 1,000 nucleotides, about 2,500 nucleotides, or about 5,000 nucleotides. In some embodiments, a probe includes from about 500 nucleotides to about 2,500 nucleotides.

A probe can further include a detectable label, e.g., a radioactive label, a biotinylated label, a fluorophore (TEXAS-RED®, fluorescein isothiocyanate, etc.). The detectable label can be covalently attached directly to the probe oligonucleotide, e.g., located at the probe's 5' end or at the probe's 3' end. A probe including a fluorophore may also further include a quencher, e.g., BLACK HOLE QUENCHER®, IOWA BLACK™, etc.

As used herein, the terms "sequence identity" or "identity" can be used interchangeably and refer to nucleic acid residues in two sequences that share similar base compositions when aligned for maximum correspondence over a specified comparison window for either a polynucleotide or protein fragment.

As used herein, the tam "percentage of sequence identity" refers to a value determined by comparing two optimally aligned sequences (e.g., nucleic acid sequences or amino acid sequences) over a comparison window, wherein the portion of a sequence in the comparison window may comprise additions or deletions (i.e., gaps) as compared to a reference sequence (that does not comprise additions or deletions) for optimal alignment of the two sequences. A percentage is calculated by determining the number of positions at which an identical nucleic acid or amino acid residue occurs in both sequences to yield the number of matched positions, dividing the number of matched positions by the total number of positions in the comparison window, and multiplying the result by 100 to yield the percentage of sequence identity. Methods for aligning sequences for comparison are well known. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al., (1988) *Nucleic Acids Res.* 16:10881-90; Huang et al., (1992) *Comp. Appl. Biosci.* 8:155-65; Pearson et al., (1994) *Methods Mol. Biol.* 24:307-31; Tatiana et al., (1999) *FEMS Microbiol. Lett.* 174:247-50.

The National Center for Biotechnology Information (NCBI) Basic Local Alignment Search Tool (BLAST; Altschul et al., (1990) *J. Mol. Biol.* 215:403-10) is available from several sources, including the National Center for Biotechnology Information (Bethesda, Md.), and on the internet, for use in connection with several sequence analysis programs. A description of how to determine sequence identity using this program is available on the internet under the "help" section for BLAST. For comparisons of nucleic acid sequences, the "Blast 2 sequences" function of the BLAST (Blastn) program may be employed using the default parameters. Nucleic acid sequences with even greater similarity to the reference sequences will show increasing percentage identity when assessed by this method.

As used herein, the term "operably linked" refers to a nucleic acid placed into a functional relationship with another nucleic acid. Generally, "operably linked" can mean that linked nucleic acids are contiguous. Linking can be accomplished by ligation at convenient restriction sites. If such sites do not exist, synthetic oligonucleotide adaptors or linkers are ligated or annealed to the nucleic acid and used to link the contiguous polynucleotide fragment. However, elements need not be contiguous to be operably linked.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5'-UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) *Genes & Dev.,* 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

A "DNA binding transgene" is a polynucleotide coding sequence that encodes a DNA binding protein. The DNA binding protein is subsequently able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

Examples of DNA binding proteins include; meganucleases, zinc fingers, CRISPRs and TALE binding domains that can be "engineered" to bind to a predetermined nucleotide sequence. Typically, the engineered DNA binding proteins (e.g., zinc fingers, CRISPRs, or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP, CRISPR, and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

In other examples, the DNA-binding domain of one or more of the nucleases comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al., (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al., (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (see Heuer et al., (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al. ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al., (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al. ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al., (2012) *Science* 337*, p.* 816-821, Jinek et al., (2013), eLife 2:e00471, and David Segal, (2013) eLife 2:e00563). Thus, the CRISPR/Cas system can be engineered to create a double-stranded break (DSB) at a desired target in a genome, and repair of the DSB can be influenced by the use of repair inhibitors to cause an increase in error prone repair.

In other examples, the DNA binding transgene is a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al., (1997) *Nucleic Acids Res.* 25:3379-30 3388; Dujon et al., (1989) *Gene* 82:115-118; Perler et al., (1994) *Nucleic Acids Res.* 22, 11127; Jasin (1996) *Trends Genet.* 12:224-228; Gimble et al., (1996) *J. Mol. Biol.* 263:163-180; Argast et al., (1998) *J. Mol. Biol.* 280:345-353 and the New England Biolabs catalogue. In addition, the DNA-binding specificity of horning endonucleases and meganucleases can be engineered to bind non-natural target sites. See, for example, Chevalier et al., (2002) *Molec. Cell* 10:895-905; Epinat et al., (2003) *Nucleic Acids Res.* 5 31:2952-2962; Ashworth et al., (2006) *Nature* 441:656-659; Paques et al., (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) *Cell* 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

As used herein, the term "transgene" refers to an exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, a transgene is a small RNA, such as an antisense nucleic acid sequence, wherein expression of the small RNA sequence inhibits expression of a target nucleic acid sequence. A transgene may contain regulatory sequences operably linked to the transgene (e.g., a promoter, intron, or 3'-UTR). In some embodiments, a nucleic acid of interest (or alternatively described as a gene of interest) is a transgene. However, in other embodiments, a nucleic acid of interest is an endogenous nucleic acid, wherein additional genomic copies of the endogenous nucleic acid are desired, or a nucleic acid that is in the antisense orientation with respect to the sequence of a target nucleic acid in a host organism.

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA, and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)"; "tmRNA" (a.k.a. "10S RNA," Muto et al., (1998) *Trends Biochem Sci.* 23:25-29; and Gillet et al., (2001) *Mol Microbiol.* 42:879-885); RNAi molecules including without limitation "small interfering RNA (siRNA)," "endoribonuclease-prepared siRNA (e-siRNA)," "short hairpin RNA (shRNA)," and "small temporally regulated RNA (stRNA)," "diced siRNA (d-siRNA)," and aptamers, oligonucleotides and other synthetic nucleic acids that comprise at least one uracil base.

As used herein, the term "vector" refers to a nucleic acid molecule as introduced into a cell, thereby producing a transformed cell. A vector may include nucleic acid sequences that permit it to replicate in the host cell, such as an origin of replication. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector may optionally include materials to aid in achieving entry of the nucleic acid molecule into the cell (e.g., a liposome).

As used herein, the terms "cassette," "expression cassette," and "gene expression cassette" refer to a segment of DNA that can be inserted into a nucleic acid or polynucleotide at specific restriction sites or by homologous recombination. A segment of DNA comprises a polynucleotide containing a gene of interest that encodes a small RNA or a polypeptide of interest, and the cassette and restriction sites are designed to ensure insertion of the cassette in the proper reading frame for transcription and translation. In an embodiment, an expression cassette can include a polynucleotide that encodes a small RNA or a polypeptide of interest and having elements in addition to the polynucleotide that facilitate transformation of a particular host cell. In an embodiment, a gene expression cassette may also include elements that allow for enhanced expression of a small RNA or a polynucleotide encoding a polypeptide of interest in a host cell. These elements may include, but are not limited to: a promoter, a minimal promoter, an enhancer, a response element, an intron, a 5' untranslated, a 3' untranslated region sequence, a terminator sequence, a polyadenylation sequence, and the like.

As used herein, the term "heterologous coding sequence" is used to indicate any polynucleotide that codes for, or ultimately codes for, a peptide or protein or its equivalent amino acid sequence, e.g., an enzyme, that is not normally present in the host organism and can be expressed in the host cell under proper conditions. As such, "heterologous coding sequences" may include one or additional copies of coding sequences that are not normally present in the host cell, such that the cell is expressing additional copies of a coding sequence that are not normally present in the cells. The heterologous coding sequences can be RNA or any type thereof, e.g., mRNA, DNA or any type thereof, e.g., cDNA, or a hybrid of RNA/DNA. Examples of coding sequences include, but are not limited to, full-length transcription units that comprise such features as the coding sequence, introns, promoter regions, 5'-UTR, 3□-UTRs and enhancer regions.

"Heterologous coding sequences" also includes the coding portion of the peptide or enzyme, i.e., the cDNA or mRNA sequence, of the peptide or enzyme, as well as the coding portion of the full-length transcriptional unit, i.e., the gene comprising introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences can have a deletion of one or more amino acids, with the deletion being N-terminal, C-terminal or internal. Truncated forms are envisioned as long as they have the catalytic capability indicated herein.

As used herein, the term "control" refers to a sample used in an analytical procedure for comparison purposes. A control can be "positive" or "negative." For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes plants and plant parts including, but not limited to, plant cells and plant tissues such as leaves, stems, roots, flowers, pollen, and seeds. A class of plant that can be used in the present invention is generally as broad as the class of higher and lower plants amenable to mutagenesis including angiosperms, gymnosperms, ferns and multicellular algae. Thus, "plant" includes dicot and monocot plants. Examples of dicotyledonous plants include tobacco, *Arabidopsis*, soybean, tomato, papaya, canola, sunflower, cotton, alfalfa, potato, grapevine, pigeon pea, pea, *Brassica*, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledonous plants include corn, rice, wheat, sugarcane, barley, rye, sorghum, orchids, bamboo, banana, cattails, lilies, oat, onion, millet, and triticale.

As used herein, the term "plant material" refers to leaves, stems, roots, flowers or flower parts, fruits, pollen, egg cells, zygotes, seeds, cuttings, cell or tissue cultures, or any other part or product of a plant. In an embodiment, plant material includes cotyledon and leaf. In an embodiment, plant material includes seed, embryo, or ovule. In an embodiment, plant material includes root tissues and other plant tissues located underground.

As used herein, the term "selectable marker gene" refers to a gene that is optionally used in plant transformation to, for example, protect plant cells from a selective agent or provide resistance/tolerance to a selective agent. In addition, "selectable marker gene" is meant to encompass reporter genes. Only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding □-glucuronidase (GUS), luciferase, green fluorescent protein (GFP), yellow fluorescent protein (YFP), DsRed, □-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, □-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the term "detecting" is used in the broadest sense to include both qualitative and quantitative measurements of a specific molecule, for example, measurements of a specific polypeptide.

Unless otherwise specifically explained, all technical and scientific terms used herein have the same meaning as commonly understood by those of ordinary skill in the art that this disclosure belongs. Definitions of common terms in molecular biology can be found in, for example: Lewin, Genes V, Oxford University Press, 1994; Kendrew et al. (eds.), The Encyclopedia of Molecular Biology, Blackwell Science Ltd., 1994; and Meyers (ed.), Molecular Biology and Biotechnology: A Comprehensive Desk Reference, VCH Publishers, Inc., 1995.

Regulatory Elements

Plant promoters used for basic research or biotechnological applications are generally unidirectional, directing the expression of a transgene that has been fused at its 3' end (downstream). It is often necessary to robustly express transgenes within plants for metabolic engineering and trait stacking. In addition, multiple novel promoters are typically required in transgenic crops to drive the expression of multiple genes. Disclosed, herein is a promoter that can direct the expression of a first gene that has been fused at its 3' end (downstream).

Development of transgenic products is becoming increasingly complex, which requires robustly expressing transgenes and stacking multiple transgenes into a single locus. Traditionally, each transgene requires a unique promoter for expression wherein multiple promoters are required to express different transgenes within one gene stack. With an increasing size of gene stacks, this frequently leads to repeated use of the same promoter to obtain similar levels of expression patterns of different transgenes for expression of a single polygenic trait. Multi-gene constructs driven by the same promoter are known to cause gene silencing resulting in less efficacious transgenic products in the field. Excess of transcription factor (TF)-binding sites due to promoter repetition can cause depletion of endogenous TFs leading to transcriptional inactivation. The silencing of transgenes will likely undesirably affect performance of a transgenic plant produced to express transgenes. Repetitive sequences within a transgene may lead to gene intra-locus homologous recombination resulting in polynucleotide rearrangements.

Tissue specific (i.e., tissue-preferred) or organ specific promoters drive gene expression in a certain tissue such as in the ovule, embryo, seed, kernel, root, leaf or tapetum of the plant. Tissue and developmental stage specific promoters derive the expression of genes, which are expressed in particular tissues or at particular time periods during plant development. Tissue specific promoters are required for certain applications in the transgenic plants industry and are desirable as they permit specific expression of heterologous genes in a tissue and/or developmental stage selective manner, indicating expression of the heterologous gene differentially at a various organs, tissues and/or times, but not in other. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Another application is the desirability of using tissue specific promoters, e.g., such that would confine the expression of the transgenes encoding an agronomic trait in developing xylem. Another application is for driving expression of a transgene within a seed, ovule, or embryo. One particular problem remaining in the identification of tissue specific promoters is how to identify the potentially most important genes and their corresponding promoters, and to relate these to specific developmental properties of the cell. Another problem is to clone all relevant cis-acting transcriptional control elements so that the cloned DNA fragment drives transcription in the wanted specific expression pattern. A particular problem is to identify tissue-specific promoters, related to specific cell types, developmental stages and/or functions in the plant that are not expressed in other plant tissues.

Provided are methods and constructs using *Brassica napus* GALE1 gene promoter regulatory elements to express transgenes in plant. In an embodiment, a promoter can be a *Brassica napus* GALE1 gene promoter of:

```
                                          (SEQ ID NO: 1)
caacaaaaatgcactttttcgccaaaaatacatttacttcaaaaaccgca

aaaatattttctgccaaacccgtaaaaatactatttttctgccgaaacgt

aaaaaaaaatatttaattattttattaacaagtccacttggatgtagat

gaaaatttaaaaaatgaaaagcaaacgaacatagttgcattcagatgatt

catctggatgcatggacgaaatgaagaaacgaacaacacccatatagagc

atctggataagacatctagatggatcattacaaaagaacagggcctaaac

atgtgagatgtttgaagcaatcagtcaaaagtaaccaccaaatcgaatta

tgaaagcgttgattggatggacaagtttaacaaccattgtttgattggac

aacgccgttatctaaacttttagtgtgctgtgtacatcattactatgaat

cagttagttaaaaatattatggtcagtgaatgacagtaagattacttcag

aacttgagagatttaccgcaaaaagaaacacaataacgcgtaggaaaaat

atcctctgattttgcaattattctcgtagatttggttatcagtaggtatc

acgttttacaaaaatagaattacaatacatgccgcaagaaaaagactact

ctttttaatttccccaatttggttatcagtattcagtaagtttcacattt

ttacaaaaatataaattaaaatacatactgcaagaaaaatactttttttaa

tttcgccaatttggttatcagtagttttcacatttttacaaaaatataat

taaaatataaactgcaacaaaaagacttatctttttaatttccccaattt

ggttatcagtattcagtaggtttcacatttacaaaaatattattaaaata

catactgcaagaaacatacctttttaatttcgccaatctggttatcagta

gttttcacatttttacaaaaatagaattaaaatacaaactgcaacaaaaa

gacttatctttttaatttccaccaataagttatttatttatttaatcctc

ccgtgaggaaaaagacaagattgaggatgaatatacgtaactgaaaattg

aggaaacagagccatcaacctacaacacggatgatcatcatcatcactct

ctgccgcctttaaatagaaaccaacaaagacattcttgagcccacactca

ctcattcctatttcttcgattgcgtgccttccttccacttatctacttgt

atcccacaaaaagctacttaataccatttaataaagaccccaactttctt

gtgtcttctctcttatcatcttcgctgtgatctctctgtctccctctctc
```

-continued

```
ttatccaaaagattagtataaaaggatcgatattccttgtgggacttcca

taaaacttcgattctcgact.
```

In an embodiment, a gene expression cassette comprises a promoter. In an embodiment, a promoter can be a *Brassica napus* GALE1 gene promoter of the subject disclosure. In an embodiment, a gene expression cassette comprises a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1. In an embodiment, a gene expression cassette comprises a *Brassica napus* GALE1 gene promoter that is operably linked to a transgene. In an embodiment, a gene expression cassette comprising the *Brassica napus* GALE1 gene promoter may drive expression of two or more transgenes. In an illustrative embodiment, a gene expression cassette comprises a *Brassica napus* GALE1 gene promoter that is operably linked to a transgene, wherein the transgene can be an insecticidal resistance transgene, a herbicide tolerance transgene, a nitrogen use efficiency transgene, a water use efficiency transgene, a nutritional quality transgene, a DNA binding transgene, a selectable marker transgene, or combinations thereof.

Transgene expression may also be regulated by a 3'-untranslated gene region (i.e., 3'-UTR) located downstream of the gene's coding sequence. Both a promoter and a 3'-UTR can regulate transgene expression. While a promoter is necessary to drive transcription, a 3'-UTR gene region can terminate transcription and initiate polyadenylation of a resulting mRNA transcript for translation and protein synthesis. A 3'-UTR gene region aids stable expression of a transgene. In an embodiment, a 3'-UTR can be a *Brassica napus* GALE1 gene 3'-UTR of:

```
                                          (SEQ ID NO: 2)
actttactctttctctctaatcgctcaatatacaaaagaaaagtgtttac

atacacacatcatatatagtttgatttagtttccatgtaaccgaacgggt

ctgtttacttctatgaataaaatagctagttgatgattctgttgattgat

acactctatggatagttcaagattaattacaatccaacgatgatagtatc

aaatagagcccaccagatcaagaaagcatactccagaagatttgttcaat

ctaccatcagataacatatcaataaccatcttcatggtggaaccatctgc

agcaaacccacacctcttcatttatctatgagttcaactgaagcgactac

accactacctccgagatgaactcggatcagtgtgttgtatgtacactcat

ttggcgcaatcccatcctcctctcccatctttttaaacaacatatccgct

tcagacagtgagcctttcttacacagtcctgcaatcattatggta.
```

In an embodiment, a gene expression cassette comprises a 3'-UTR. In an embodiment, a 3'-UTR can be a *Brassica napus* GALE1 gene 3'-UTR. In an embodiment, a gene expression cassette comprises a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:2. In an embodiment, a gene expression cassette comprises a *Brassica napus* GALE1 gene 3'-UTR that is operably linked to a transgene. In an illustrative embodiment, a gene expression cassette comprises a 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a gene expression cassette comprises a promoter and a 3'-UTR purified from the *Brassica napus* GALE1 gene. In an embodiment, a gene expression cassette comprises: a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, and/or, b) a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:2.

For example, a gene expression cassette may include both a promoter and a 3'-UTR wherein the promoter is a polynucleotide of SEQ ID NO:1, and the 3'-UTR is a polynucleotide of SEQ ID NO:2. A promoter and 3'-UTR can be operably linked to different transgenes within a gene expression cassette when a gene expression cassette includes one or more transgenes. In an illustrative embodiment, a gene expression cassette comprises a *Brassica napus* GALE1 gene promoter (SEQ ID NO:1) that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Brassica napus* GALE1 gene 3'-UTR (SEQ ID NO:2) that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, a vector comprises a gene expression cassette, as disclosed herein. In an embodiment, a vector can be a plasmid, a cosmid, a bacterial artificial chromosome (BAC), a bacteriophage, a virus, or an excised polynucleotide fragment for use in transformation or gene targeting such as a donor DNA.

In an embodiment, a cell or plant comprises a gene expression cassette, as disclosed herein. In an embodiment, a cell or plant comprises a vector comprising a gene expression cassette, as disclosed herein. In an embodiment, a vector can be a plasmid, a cosmid, a bacterial artificial chromosome (BAC), a bacteriophage, or a virus. Thereby, a cell or plant comprising a gene expression cassette, as disclosed herein, is a transgenic cell or transgenic plant, respectively. In an embodiment, a transgenic plant can be a monocotyledonous plant. In an embodiment, a transgenic monocotyledonous plant can be, but is not limited to, maize, wheat, rice, sorghum, oats, rye, bananas, sugar cane, and millet. In an embodiment, a transgenic plant can be a dicotyledonous plant. In an embodiment, a transgenic dicotyledonous plant can be, but is not limited to, soybean, cotton, sunflower, and canola. An embodiment also includes a transgenic seed from a transgenic plant, as disclosed herein.

In an embodiment, a gene expression cassette includes two or more transgenes. The two or more transgenes may be operably linked to a *Brassica napus* GALE1 gene promoter or 3'-UTR, as disclosed herein. In an embodiment, a gene expression cassette includes one or more transgenes. In an embodiment with one or more transgenes, at least one transgene is operably linked to a *Brassica napus* GALE1 gene promoter or 3'-UTR or the subject disclosure.

Selectable Markers

Various selectable markers, also described as reporter genes, can be incorporated into a chosen expression vector to allow for identification and selection of transformed plants ("transformants"). Many methods are available to confirm expression of selectable markers in transformed plants, including, for example, DNA sequencing and PCR (polymerase chain reaction), Southern blotting, RNA blotting, immunological methods for detection of a protein expressed from the vector, eg., precipitated protein that mediates phosphinothricin resistance, or visual observation of other proteins such as reporter genes encoding □-glucuronidase (GUS), luciferase, green fluorescent protein (GFP), yellow fluorescent protein (YFP), red fluorescent protein (DsRed), □-galactosidase, chloramphenicol acetyltransferase (CAT), alkaline phosphatase, and the like (see Sambrook, et al., Molecular Cloning: A Laboratory Manual, Third Edition, Cold Spring Harbor Press, N.Y., 2001, the content is incorporated herein by reference in its entirety).

Selectable marker genes are utilized for selection of transformed cells or tissues. Selectable marker genes include genes encoding antibiotic resistance, such as those encoding neomycin phosphotransferase II (NptII) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding pat or DSM-2, a nitrilase, an aad-1 or an aad-12 gene, which detoxifies the respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including Haloxyfop, Diclofop, Fenoxyprop, Fluazifop, Quizalofop) include genes of acetyl coenzyme A carboxylase (ACCase)—Accl-S1, Accl-S2 and Accl-S3. In an embodiment, herbicides can inhibit photosynthesis, including triazine (psbA and Is+ genes) or benzonitrile (nitrilase gene).

In an embodiment, selectable marker genes include, but are not limited to, genes encoding: neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA).

An embodiment also includes genes encoding resistance to: 2,4-D; chloramphenicol; methotrexate; hygromycin; spectinomycin; bromoxynil; glyphosate; and phosphinothricin.

The above list of selectable marker genes is not meant to be limiting. Any reporter or selectable marker gene are encompassed by the present invention.

Selectable marker genes are synthesized for optimal expression in a plant. For example, in an embodiment, a coding sequence of a gene has been modified by codon optimization to enhance expression in plants. A selectable marker gene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a selectable marker gene is designed to be expressed in plants at a higher level resulting in higher transformation efficiency. Methods for plant optimization of genes are well known. Guidance regarding the optimization and manufacture of synthetic polynucleotide sequences can be found in, for example, WO2013016546, WO2011146524, WO1997013402, U.S. Pat. No. 6,166,302, and U.S. Pat. No. 5,380,831, herein incorporated by reference.

Transgenes

The disclosed methods and compositions can be used to express polynucleotide gene sequences within the plant genome. Accordingly, expression of genes encoding herbicide tolerance, insect resistance, nutrients, antibiotics or therapeutic molecules can be driven by a plant promoter.

In one embodiment the *Brassica napus* GALE1 gene regulatory element of the subject disclosure is combined or operably linked with gene encoding polynucleotide sequences that provide resistance or tolerance to glyphosate or another herbicide, and/or provides resistance to select insects or diseases and/or nutritional enhancements, and/or improved agronomic characteristics, and/or proteins or other products useful in feed, food, industrial, pharmaceutical or other uses. The transgenes can be "stacked" with two or more nucleic acid sequences of interest within a plant genome. Stacking can be accomplished, for example, via conventional plant breeding using two or more events, transformation of a plant with a construct which contains the sequences of interest, re-transformation of a transgenic plant, or addition of new traits through targeted integration via homologous recombination.

Such polynucleotide sequences of interest include, but are not limited to, those examples provided below:

1. Genes or Coding Sequence (e.g., iRNA) that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium flavum* (Jones et al., 1994 Science 266:789), tomato Pto gene, which encodes a protein kinase, for resistance to *Pseudomonas syringae* pv. tomato (Martin et al., 1993 *Science* 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt □-endotoxin gene (Geiser et al., 1986 Gene 48:109), and a vegetative insecticidal (VIP) gene (see, e.g., Estruch et al., (1996) Proc. Natl. Acad. Sci. 93:5389-94). Moreover, DNA molecules encoding □-endotoxin genes can be purchased from American Type Culture Collection (Rockville, Md.), under ATCC accession numbers 40098, 67136, 31995 and 31998.

(C) A lectin, such as, nucleotide sequences of several Clivia miniata mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an □-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691), and parsley ubi4-2 polyubiquitin gene (Kawalleck et al., 1993 Plant Molec. Biol. 21:673).

(K) A molecule that stimulates signal transduction. Examples of such molecules include nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-□ lytic peptide analog (Jaynes et al., 1993 Plant Sci. 89:43) which renders transgenic tobacco plants resistant to Pseudomonas solanacearum.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al., (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al., (1994) Abstract #497, Seventh Intl. Symposium on Molecular Plant-Microbe Interactions shows enzymatic inactivation in transgenic tobacco via production of single-chain antibody fragments.

(P) A virus-specific antibody. See, for example, Tavladoraki et al., (1993) Nature 266:469, which shows that transgenic plants expressing recombinant antibody genes are protected from virus attack.

(Q) A developmental-arrestive protein produced in nature by a pathogen or a parasite. Thus, fungal endo □-1,4-D polygalacturonases facilitate fungal colonization and plant nutrient release by solubilizing plant cell wall homo-□-1,4-D-galacturonase (Lamb et al., 1992) Bio/Technology 10:1436. The cloning and characterization of a gene which encodes a bean endopolygalacturonase-inhibiting protein is described by Toubart et al., (1992 Plant J. 2:367).

(R) A developmental-arrestive protein produced in nature by a plant, such as the barley ribosome-inactivating gene that provides an increased resistance to fungal disease (Longemann et al., 1992). Bio/Technology 10:3305.

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al. U.S. Pat. No. 6,506,559; Graham et al. U.S. Pat. No. 6,573,099.

2. Genes that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for mutant acetolactate synthase (ALS) (Lee et al., 1988 EMBO J. 7:1241) also known as acetohydroxyacid synthase (AHAS) enzyme (Mild et al., 1990 Theor. Appl. Genet. 80:449).

(B) One or more additional genes encoding resistance or tolerance to glyphosate imparted by mutant EPSP synthase and aroA genes, or through metabolic inactivation by genes such as DGT-28, 2mEPSPS, GAT (glyphosate acetyltransferase) or GOX (glyphosate oxidase) and other phosphono compounds such as glufosinate (pat, bar, and dsm-2 genes), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al., (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al., (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al., (1991) Plant Cell 3:169 describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al., (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2phenyl) propane-1,3-dione, triketones (EP625505, EP625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the □-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the □-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (see Brussian et al., (1989) EMBO J. 1989, 8(4): 1237-1245.

3. Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., 1992) Proc. Nat. Acad. Sci. USA 89:2624.

(B) Decreased Phytate Content (1) Introduction of a phytase-encoding gene, such as the *Aspergillus niger* phytase gene (Van Hartingsveldt et al., 1993 Gene 127:87), enhances breakdown of phytate, adding more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, *Streptococcus* mucus fructosyltransferase gene (Shiroza et al., 1988) *J. Bacteriol.* 170:810, *Bacillus subtilis* levansucrase gene (Steinmetz et al., 1985 Mol. Gen. Genel. 200:220), *Bacillus licheniformis* □-amylase (Pen et al., 1992 Bio/Technology 10:292), tomato invertase genes (Elliot et al., 1993), barley amylase gene (Sogaard et al., 1993 J. Biol. Chem. 268:22480), and maize endosperm starch branching enzyme II (Fisher et al., 1993 Plant Physiol. 102:10450).

Transformation

Suitable methods for transformation of plants include any method that DNA can be introduced into a cell, for example, and without limitation: electroporation (see, e.g., U.S. Pat. No. 5,384,253); micro-projectile bombardment (see, e.g., U.S. Pat. Nos. 5,015,580; 5,550,318; 5,538,880; 6,160,208; 6,399,861; and 6,403,865); *Agrobacterium*-mediated transformation (see, e.g., U.S. Pat. Nos. 5,635,055; 5,824,877; 5,591,616; 5,981,840; and 6,384,301); and protoplast transformation (see, e.g., U.S. Pat. No. 5,508,184). These methods may be used to stably transform or transiently transform a plant.

A DNA construct may be introduced directly into the genomic DNA of the plant cell using techniques such as agitation with silicon carbide fibers (see, e.g., U.S. Pat. Nos. 5,302,523 and 5,464,765), or the DNA constructs can be introduced directly to plant tissue using biolistic methods, such as DNA particle bombardment (see, e.g., Klein et al., (1987) *Nature* 327:70-73). Alternatively, the DNA construct can be introduced into the plant cell via nanoparticle transformation (see, e.g., U.S. Patent Publication No. 2009/0104700, incorporated herein by reference in its entirety).

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, see, e.g., Chung et al., (2006) *Trends Plant Sci.* 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797; 5,159,135; 5,004,863; and 6,624,344; techniques for transforming *Brassica* plants in particular are described, for example, in U.S. Pat. No. 5,750,871; techniques for transforming soy bean are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a desired nucleic acid comprising constructs provided in regenerating plants, a variety of assays may be performed. Such assays may include: molecular biological assays, such as Southern and Northern blotting and PCR; biochemical assays, such as detecting the presence of a protein product, e.g., by immunological methodology (ELISA, western blots, and/or LC-MS MS spectrophotometry) or by enzymatic function; plant part assays, such as leaf or root assays; and/or analysis of the phenotype of the whole regenerated plant.

Transgenic events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al., (2002) Plant J. 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example, and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. Primers may be used in conjunction with primers described herein. Oligonucleotide primers may be synthesized according to a desired sequence and are commercially available (e.g., from Integrated DNA Technologies, Inc., Coralville, Iowa). Amplification may be followed by cloning and sequencing, or by direct sequence analysis of amplification products. In an embodiment, oligonucleotide primers specific for the gene target are employed in PCR amplifications.

Method of Expressing a Transgene

In an embodiment, a method of expressing at least one transgene in a plant comprises growing a plant comprising a *Brassica napus* GALE1 gene promoter operably linked to at least one transgene. In an embodiment, a method of expressing at least one transgene in a plant comprising growing a plant comprising a *Brassica napus* GALE1 gene 3'-UTR operably linked to at least one transgene. In an embodiment, a method of expressing at least one transgene in a plant comprises growing a plant comprising a *Brassica napus* GALE1 gene promoter and 3'-UTR operably linked to at least one transgene.

In an embodiment, a method of expressing at least one transgene in a plant tissue or plant cell comprising culturing a plant tissue or plant cell comprising a *Brassica napus* GALE1 gene promoter operably linked to at least one transgene. In an embodiment, a method of expressing at least one transgene in a plant tissue or plant cell comprising culturing a plant tissue or plant cell comprising a *Brassica napus* GALE1 gene 3'-UTR operably linked to at least one transgene. In an embodiment, a method of expressing at least one transgene in a plant tissue or plant cell comprising culturing a plant tissue or plant cell comprising a *Brassica napus* GALE1 gene promoter and a *Brassica napus* GALE1 gene 3'-UTR operably linked to at least one transgene.

In an embodiment, a method of expressing at least one transgene in a plant comprises growing a plant comprising a gene expression cassette comprising a *Brassica napus* GALE1 gene promoter operably linked to at least one transgene. In an embodiment, a method of expressing at least one transgene in a plant comprises growing a plant comprising a gene expression cassette comprising a *Brassica napus* GALE1 gene 3'-UTR operably linked to at least one transgene. In an embodiment, a method of expressing at least one transgene in a plant comprises growing a plant comprising a gene expression cassette comprising a *Brassica napus* GALE1 gene promoter and a *Zea mays* chlorophyll a/b binding gene 3'-UTR operably linked to at least one transgene.

In an embodiment, a method of expressing at least one transgene in a plant tissue or plant cell comprises culturing a plant tissue or plant cell comprising a gene expression cassette a *Brassica napus* GALE1 gene promoter operably linked to at least one transgene. In an embodiment, a method of expressing at least one transgene in a plant tissue or plant cell comprises culturing a plant tissue or plant cell comprising a gene expression cassette a *Brassica napus* GALE1 gene 3'-UTR operably linked to at least one transgene. In an embodiment, a method of expressing at least one transgene in a plant tissue or plant cell comprises culturing a plant tissue or plant cell comprising a gene expression cassette a *Brassica napus* GALE1 gene promoter and a *Brassica napus* GALE1 gene 3'-UTR operably linked to at least one transgene.

In an embodiment, a plant, plant tissue, or plant cell comprises a *Brassica napus* GALE1 gene promoter (also including an upstream-promoter). In an embodiment, a *Brassica napus* GALE1 gene promoter can be SEQ ID NO:1. In an embodiment, a plant, plant tissue, or plant cell comprises a gene expression cassette comprising *Brassica napus* GALE1 gene promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1. In an embodiment, a plant, plant tissue, or plant cell comprises a gene expression cassette comprising a *Brassica napus* GALE1 gene promoter that is operably linked to a transgene. In an illustrative embodiment, a plant, plant tissue, or plant cell comprises a gene expression cassette comprising a *Brassica napus* GALE1 gene promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a *Brassica napus* GALE1 gene 3'-UTR. In an embodiment, a plant, plant tissue, or plant cell comprises a gene expression cassette comprising a *Brassica napus* GALE1 gene 3'-UTR. In an embodiment, the *Brassica napus* GALE1 gene 3'-UTR is a polynucleotide of SEQ ID NO:2. In an embodiment, a plant, plant tissue, or plant cell comprises a gene expression cassette comprising a *Brassica napus* GALE1 gene 3'-UTR, wherein the *Brassica napus* GALE1 gene 3'-UTR is at least 80%, 85%, 90%, 91%, 92%, 93%, 94%, 95%, 96%, 97%, 98%, 99%, 99.5%, 99.8%, or 100% identical to SEQ ID NO:2. In an embodiment, a gene expression cassette comprises a *Brassica napus* GALE1 gene 3'-UTR that is operably linked to a promoter, wherein the promoter is a *Brassica napus* GALE1 gene promoter, or a promoter that originates from a plant (e.g., *Arabidopsis thaliana* ubiquitin 10 promoter), a virus (e.g., Cassava vein mosaic virus promoter) or a bacteria (e.g., *Agrobacterium tumefaciens* delta mas). In an embodiment, a plant, plant tissue, or plant cell comprises a gene expression cassette comprising a *Brassica napus* GALE1 gene 3'-UTR that is operably linked to a transgene. In an illustrative embodiment, a plant, plant tissue, or plant cell comprising a gene expression cassette comprising a *Brassica napus* GALE1 gene 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a *Brassica napus* GALE1 gene promoter and *Brassica napus* GALE1 gene 3'-UTR that are operably linked to a transgene. The promoter and 3'-UTR can be operably linked to different transgenes within a gene expression cassette when a gene expression cassette includes two or more transgenes. In an illustrative embodiment, a gene expression cassette comprises a *Brassica napus* GALE1 gene promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Brassica napus* GALE1 gene 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, transgene expression using methods described herein is expressed within a plant's ovule and seed tissues. In an embodiment, transgene expression includes more than one transgene expressed in the plant's ovule and seed tissues. In an embodiment, a method of growing a transgenic plant as described herein includes ovule and seed-preferred transgene expression. In an embodiment, a method of expressing a transgene in a plant tissue or plant cell includes ovule and seed-preferred tissues and ovule and seed-preferred cells. In an embodiment, the ovule and seed-preferred expression includes dicotyledonous leaf and stem-preferred expression.

In a further embodiment, transgene expression using methods described herein is expressed within above ground plant tissues (e.g., ovule or seed). In an embodiment, transgene expression includes more than one transgene expressed in above ground plant tissues such as ovule or seed. In other embodiments, the expression of the transgene is within the endosperm tissue of seeds. In an embodiment, a method of growing a transgenic plant as described herein includes above ground plant tissues transgene expression. In an embodiment, a method of expressing a transgene in a plant tissue or plant cell above ground plant tissues and above ground plant cells. In an embodiment, the above ground plant tissue expression includes dicotyledonous above ground plant tissue expression.

In an embodiment, a plant, plant tissue, or plant cell comprises a vector comprising a *Brassica napus* GALE1 gene promoter, or 3'-UTR regulatory element, as disclosed herein. In an embodiment, a plant, plant tissue, or plant cell comprises a vector comprising a *Brassica napus* GALE1 gene promoter, or 3'-UTR regulatory element, as disclosed herein, operably linked to a transgene. In an embodiment, a plant, plant tissue, or plant cell comprises a vector comprising a gene expression cassette, as disclosed herein. In an embodiment, a vector can be a plasmid, a cosmid, a bacterial artificial chromosome (BAC), a bacteriophage, or a virus fragment.

In an embodiment, a plant, plant tissue, or plant cell according to the methods disclosed herein can be monocotyledonous. The monocotyledon plant, plant tissue, or plant cell can be, but not limited to, corn, rice, wheat, sugarcane, barley, rye, sorghum, orchids, bamboo, banana, cattails, lilies, oat, onion, millet, and triticale.

In an embodiment, a plant, plant tissue, or plant cell according to the methods disclosed herein can be dicotyledonous. The dicotyledon plant, plant tissue, or plant cell can be, but is not limited to, rapeseed, canola, Indian mustard, Ethiopian mustard, soybean, sunflower, and cotton.

With regard to the production of genetically modified plants, methods for the genetic engineering of plants are well known in the art. For instance, numerous methods for plant transformation have been developed, including biological and physical transformation protocols for dicotyledonous plants as well as monocotyledonous plants (e.g., Goto-Fumiyuki et al., *Nature Biotech* 17:282-286 (1999); Mild et al., Methods in Plant Molecular Biology and Biotechnology, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed cells can also be identified by screening for the activities of any visible marker genes (e.g., the yfp, gfp, □-glucuronidase, luciferase, B or Cl genes) that may be present on the recombinant nucleic acid constructs. Such selection and screening methodologies are well known to those skilled in the art.

Physical and biochemical methods also may be used to identify plant or plant cell transformants containing inserted gene constructs. In certain embodiments, the disclosure relates to a method that includes confirming a modification of genomic DNA such as the a gene expression cassette inserted into the genome of plants. In certain embodiments, the method of confirming such a modification of the genome includes confirmation by a PCR based assay, Southern blot assay, Northern blot assay, protein expression assay, Western blot assay, ELISA assay, or Next Generation Sequencing assay.

Accordingly, a modification of genomic DNA such as a gene expression cassette inserted into the genome of plants can be confirmed in a variety of ways, including using a primer or probe of the sequence. In certain embodiments, the stably integrated transgene may be detected based on the constitutive or selective expression of the transgene in some tissues of the plant or at some developmental stages, or the transgene may be expressed in substantially all plant tissues, substantially along its entire life cycle.

Confirmation of a gene expression cassette inserted into the genome of plants may be carried out by any suitable method of amplification. See generally, Kwoh et al., Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad Sci. USA 86, 1173-1177 (1989)), self-sustained sequence replication (or "3SR") (see J. Guatelli et al., Proc. Natl. Acad. Sci. USA 87, 1874-1878 (1990)), the Q□ replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is generally preferred.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity.

As used herein, the term "polymerase chain reaction" and "PCR" generally refers to the method for increasing the concentration of a segment of a target sequence in a mixture of genomic DNA without cloning or purification (U.S. Pat. Nos. 4,683,195; 4,683,202; and 4,965,188; herein incorporated by reference). This process for amplifying the target sequence comprises introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and, therefore, this length is a controllable parameter. By virtue of the repeating aspect of the process, the method is referred to as the "polymerase chain reaction" (hereinafter "PCR"). Because the desired amplified segments of the target sequence become the predominant sequences (in tams of concentration) in the mixture, they are said to be "PCR amplified.

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

In an embodiment, the amplification reaction is quantified. In other embodiments, the amplification reaction is quantitated using a signature profile, in which the signature profile is selected from the group consisting of a melting temperature or a fluorescence signature profile.

The nucleic acid molecule of embodiments of the disclosure, or segments thereof, can be used as primers for PCR amplification. In performing PCR amplification, a certain degree of mismatch can be tolerated between primer and template. Therefore, mutations, deletions, and insertions (especially additions of nucleotides to the 5' or 3' end) of the exemplified primers fall within the scope of the subject disclosure. Mutations, insertions, and deletions can be produced in a given primer by methods known to an ordinarily skilled artisan.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar assays are a method of detecting and quantifying the presence of a DNA sequence. Briefly, the genomic DNA sample comprising the a gene expression cassette inserted into the genome of plants is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the donor DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the donor DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX GREEN®, SYBR GREEN I®, SYTO11®, SYTO12®, SYTO13®, BOBO®, YOYO®, and TOTO®. In one embodiment, a second fluorescent DNA dye is SYTO13® used at less than 10 μM, less than 4 μM, or less than 2.7 μM.

In further embodiments, Next Generation Sequencing (NGS) can be used for confirming a gene expression cassette inserted into the genome of plants. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX from 454 Life Sciences/Roche, the Illumina Genome Analyser from Solexa and Applied Biosystems' SOLiD (acronym for: "Sequencing by Oligo Ligation and Detection"). In addition, there are two single molecule sequencing methods that are currently being developed. These include the true Single Molecule Sequencing (tSMS) from Helicos Bioscience and the Single Molecule Real Time sequencing (SMRT) from Pacific Biosciences.

The Genome Sequencher FLX which is marketed by 454 Life Sciences/Roche is a long read NGS, which uses emulsion PCR and pyrosequencing to generare sequencing reads. DNA fragments of 300-800 bp or libraries containing fragments of 3-20 kbp can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser which is marketed by Solexa is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems is a short read technology. This NGS technology uses fragmented double stranded DNA that are up to 10 kbp in length. The system uses sequencing by ligation of dye-labelled oligonucleotide primers and emulsion PCR to generate one billion short reads that result in a total sequence output of up to 30 gigabases per run.

tSMS of Helicos Bioscience and SMRT of Pacific Biosciences apply a different approach which uses single DNA molecules for the sequence reactions. The tSMS Helicos system produces up to 800 million short reads that result in 21 gigabases per run. These reactions are completed using fluorescent dye-labelled virtual terminator nucleotides that is described as a "sequencing by synthesis" approach.

The SMRT Next Generation Sequencing system marketed by Pacific Biosciences uses a real time sequencing by synthesis. This technology can produce reads of up to 1000 bp in length as a result of not being limited by reversible terminators. Raw read throughput that is equivalent to one-fold coverage of a diploid human genome can be produced per day using this technology.

In another embodiment, the confirmation of a gene expression cassette inserted into the genome of plants can be completed using blotting assays, including Western blots, Northern blots, and Southern blots. Such blotting assays are commonly used techniques in biological research for the identification and quantification of biological samples. These assays include first separating the sample components in gels by an electrophoretic method, followed by transfer of the electrophoretically separated components from the gels to transfer membranes that are made of materials such as nitrocellulose, polyvinylidene fluoride (PVDF), or Nylon. Analytes can also be directly spotted on these supports or directed to specific regions on the supports by applying vacuum, capillary action, or pressure, without prior separation. The transfer membranes are then commonly subjected to a post-transfer treatment to enhance the ability of the analytes to be distinguished from each other and detected, either visually or by automated readers.

In a further embodiment the confirmation of a gene expression cassette inserted into the genome of plants can be completed using an ELISA assay, which uses a solid-phase enzyme immunoassay to detect the presence of a substance, usually an antigen, in a liquid sample or wet sample. Antigens from the sample are attached to a surface of a plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate.

The present disclosure also encompasses seeds of the transgenic plants described above wherein the seed comprises the transgene or gene expression cassette. The present disclosure further encompasses the progeny, clones, cell lines or cells of the transgenic plants described above wherein said progeny, clone, cell line or cell comprise the transgene or gene construct.

While the invention has been described with reference to specific methods and embodiments, it will be appreciated that various modifications and changes may be made without departing from the invention.

EXAMPLES

Example 1

Identification of Regulatory Elements from *Brassica napus*

*Brassica napus* gene regulatory elements were identified via a microarray profiling approach. The regulatory elements were then isolated and cloned to characterize the expression profile of the regulatory elements for use in transgenic plants. Transgenic *Arabidopsis* lines stably transformed with a Phiyfp gene and a pat selectable marker gene were produced, and the transgene expression levels and tissue specificity was assessed. As such, *Brassica napus* regulatory elements were identified and characterized. Disclosed for the first time are promoter and 3'-UTR regulatory elements for use in gene expression constructs.

Microarray Profiling Approach

Developing *Brassica napus* seeds were collected from both a transgenic homozygote line and untransformed wild-type plants at 15, 20, 25, 30, 35 and 42 days after pollination (DAP). Next, the seeds were analyzed via a single-color, global gene expression profiling design to determine global levels of gene expression for each of the defined time points.

Three identical replicates of individual 60-mer oligonucleotide arrays (Agilent Technologies Inc., Santa Clara, Calif.) were hybridized with amplified, Cy3 labeled cRNA from each sample. A custom designed 60-mer comprehensive transcriptome-wide canola oligonucleotide array (eArray, Agilent Technologies, Inc., Santa Clara, Calif.) was used to carry out the hybridizations. The oligonucleotide array contains more than 37,000 different canola transcripts obtained from public data sources (Agilent Technologies, Inc., Santa Clara, Calif.).

The 60-mer oligonucleotides were synthesized in-situ using the SURE-PRINT™ technology from the manufacturer (Agilent Technologies, Inc., Santa Clara, Calif.). To efficiently measure the expression levels of each transcript, the oligonucleotides present in the array were designed to be unique and specific for each target to efficiently hybridize with the predicted target sequence. Oligonucleotides that formed a duplex with more than one transcript were eliminated from the array. Each oligonucleotide also fulfilled the chemical and physical properties required for optimal performance throughout microarray processing. In addition, specific and unique oligonucleotides representing the newly introduced genes as well as several other genes of interest were also included in the custom designed canola oligonucleotide array. These criteria were used to produce the custom designed 60-mer comprehensive transcriptome-wide canola oligonucleotide array.

Samples of developing seeds were obtained at 15, 20, 25, 30, 35 and 42 days after pollination (DAP) from multiple plants of each genotype (NEX710® wildtype and AnD9DS transgenic lines). The seeds were frozen and pooled to be used as starting material for RNA isolation and purification. For labeling, a total of 1.0 μg of purified total RNA from each sample was reverse transcribed, amplified and labeled with Cy3-CTP following the Agilent One-Color Microarray-Based Gene Expression QuickAmp Labeling Protocol™ (Agilent, Santa Clara, Calif.). Oligonucleotide gene expression arrays were hybridized using the Agilent Technologies Gene Expression Hybridization Kit™ and WASH BUFFER KIT™ (Agilent, Santa Clara, Calif.). Hybridizations were carried out on a fully automated TECAN HS4800 PRO™ (TECAN, Research Triangle Park, NC) hybridization station.

After scanning and feature extraction, raw data files were uploaded into GeneSpring GX version 10.0.2™ (Agilent Technologies, Santa Clara, Calif.). Quality control on samples based on spike-in controls was performed to ensure that the generated data was of sufficient quality before generating a report by GENESPRING®. Next, the resulting data was normalized using a global percentile shift normalization method to minimize systematic non-biological differences and standardize arrays for cross comparisons. The normalized data was then filtered by selecting entities that were flagged as "Present" in every single sample under study, and eliminating entities flagged as "Marginal" or "Absent." The normalized and filtered list of entities was used as input for statistical analysis using a two-way ANOVA method with a corrected p-value cut-off of $p<0.05$ defining DAP and genotype as parameters. The global gene expression profile of *Brassica napus* seed development was defined for all time points in the study. An additional set of selection criteria was applied to identify genes that consistently expressed at high levels (>50,000 pixels/spot) in all samples during early *Brassica napus* seed development.

Additional genes were manually selected based upon gene annotation to bring the total candidate pool to 88 targets. To refine this pool, the expression level was verified against known oils biosynthetic gene expression levels with quantitative Real Time Polymerase Chain Reaction (RT-qPCR). RNA from the 15 and 20 DAP timepoints was examined, as was total RNA extracted and purified from young canola leaves. cDNA synthesis for RT-qPCR was conducted with SUPERSCRIPTIII™ (Invitrogen, Carlsbad, Calif.). Real Time PCR reactions were carried out on a LIGHTCYCLER® 480 instrument (Roche, Indianapolis, Ind.) using AbGene Absolute Blue SYBR green master Mix™ (Thermo Fisher). Primers for RT-qPCR were designed using PRIMER3™ (MIT, Cambridge, Mass.). Primers were designed to an optimal Tm of 60 C. Amplicon sizes ranged from 100-224 bp. Primers were selected to produce an amplicon in the 3' region of the transcribed target sequence. For normalization purposes, 4 endogenous oils biosynthetic genes were also measured, including BnACP05 (acyl-carrier protein), BnKCS (ketoacyl-CoA synthase), BnKASIII (ketoacyl-ACP synthase), and BnSAD (stearoyl-ACP desaturase).

To further filter the candidate pool, genes which displayed expression in early seeds higher than that of ACP05 (GenBank: X16114.1) were selected. Genes also were required to exhibit expression increases from leaf to early seed that were greater than the seed/leaf expression differential of KASII (GenBank: AF244520.1). These filters reduced the list of candidates down to a specific gene for identification of a target promoter. Accordingly, the microarray assay was used to identify promoter and 3'UTR gene regulatory elements from *Brassica napus* that highly expressed cDNA at 15 DAP, and was preferentially expressed in seed.

Example 2

Gene Regulatory Element Identification

A specific sequence was selected from the *Brassica napus* microarray generated data using the screening parameters described above. A PCR reaction was used to isolate the specific promoter and 3'UTR sequences from the *Brassica napus* c.v. Nex710. The PCR primers were designed from the expressed sequence tag contig 27160, assembled from publicly available ESTs Genbank: EV001081.1, CD813186.1, ES989902.1 and EV088583.1), and the genomic contig ctg7180009837416 from *Brassica oleracea* c.v. TO1000, identified as having homology to the EST contig 27160. The extracted promoter and 3' UTR *Brassica napus* regulatory sequences were obtained and further characterized via DNA sequencing. The promoter sequence of the *Brassica napus* gene labeled as GALE1, from the *Brassica napus* c.v. Nex710 genome is provided as a 1429 bp promoter sequence of SEQ ID NO:1. The 500 bp 3'-UTR sequence is provided below as SEQ ID NO:2.

SEQ ID NO: 1

```
caacaaaaatgcactttttcgccaaaaatacatttacttcaaaaaccgca
aaaatattttctgccaaacccgtaaaaatactatttttctgccgaaacgt
aaaaaaaaatattttaattattttattaacaagtccacttggatgtagat
gaaaatttaaaaaatgaaaagcaaacgaacatagttgcattcagatgatt
catctggatgcatggacgaaatgaagaaacgaacaacacccatatagagc
atctggataagacatctagatggatcattacaaaagaacagggcctaaac
atgtgagatgtttgaagcaatcagtcaaaagtaaccaccaaatcgaatta
tgaaagcgttgattggatggacaagtttaacaaccattgtttgattggac
```

-continued

```
aacgccgttatctaaacttttagtgtgctgtgtacatcattactatgaat
cagttagttaaaaatattatggtcagtgaatgacagtaagattacttcag
aacttgagagatttaccgcaaaaagaaacacaataacgcgtaggaaaaat
atcctctgattttgcaattattctcgtagatttggttatcagtaggtatc
acgttttacaaaaatagaattacaatacatgccgcaagaaaaagactact
ctttttaatttccccaatttggttatcagtattcagtaagtttcacattt
ttacaaaaatataaattaaaatacatactgcaagaaaaatactttttttaa
tttcgccaatttggttatcagtagttttcacatttttacaaaaatataat
taaaatataaactgcaacaaaaagacttatctttttaatttccccaattt
ggttatcagtattcagtaggtttcacatttacaaaaatattattaaaata
catactgcaagaaacatacctttttaatttcgccaatctggttatcagta
gttttcacatttttacaaaaatagaattaaaatacaaactgcaacaaaaa
gacttatctttttaatttccaccaataagttatttatttatttaatcctc
ccgtgaggaaaaagacaagattgaggatgaatatacgtaactgaaaattg
aggaaacagagccatcaacctacaacacggatgatcatcatcatcactct
ctgccgcctttaaatagaaaccaacaaagacattcttgagcccacactca
ctcattcctatttcttcgattgcgtgccttccttccacttatctacttgt
atcccacaaaaagctacttaataccatttaataaagaccccaactttctt
gtgtcttctctcttatcatcttcgctgtgatctctctgtctccctctctc
ttatccaaaagattagtataaaaggatcgatattccttgtgggacttcca
taaaacttcgattctcgact
```

SEQ ID NO: 2

```
Actttactctttctctctaatcgctcaatatacaaaagaaaagtgtttac
atacacacatcatatatagtttgcttttagtttccatgtaaccgaacggg
tctgtttacttctatgaataaaatagctagttgatgattctgttgattga
tacactctatggatagttcaagattaattacaatccaacgatgatagtat
caaatagagcccaccagatcaagaaagcatactccagaagatttgttcaa
tctaccatcagataacatatcaataaccatcttcatggtggaaccatctg
cagcaaacccacacctcttcatttcttctatgagttcaactgaagcgact
acaccactacctccgagatgaactcggatcagtgtgttgtatgtacactc
atttggcgcaatcccatcctcctctcccatctttttaaacaacatatccg
cttcagacagtgagcctttcttacacagtcctgcaatcattatggta
```

Example 3

*Brassica napus* Promoter and 3'UTR Construct

A gene expression cassette was constructed that was comprised of the full-length *Brassica napus* GALE1 gene promoter of SEQ ID NO:1, yellow fluorescent protein gene (Phiyfp; Shagin et al., (2004) *Mol Biol Evol* 21; 841-50) which contains the *Solanum tuberosum*, light specific tissue inducible LS-1 gene (ST-LS1 intron; Genbank Acc No. X04753), and the *Brassica napus* GALE1 3'UTR of SEQ ID NO:2 using standard recombinant DNA techniques. This gene expression cassette was flanked by att sites. Next, a GATEWAY® LR CLONASE II® (Life Technologies, Carlsbad, Calif.) reaction was performed with the resulting entry plasmid containing the yfp gene expression cassette, under the control of the *Brassica napus* GALE1 gene promoter and terminated by the *Brassica napus* GALE1 gene 3' UTR, and a destination vector leading to a final expression vector, pDAB113903. The destination vector contained a selectable marker cassette comprised of a pat gene (Wohlleben et al., *Gene* 70:25-37; 1988) driven by the Cassava vein mosaic virus promoter (CsVMV promoter; Verdaguer et al., *Plant Molecular Biology* 31:1129-1139; 1996) and terminated by an *Agrobacterium tumefaciens* open reading frame 1 3'-UTR (AtuORF1 3'UTR; Huang et al., *J. Bacteriol.* 172:1814-1822; 1990). The resulting construct, pDAB113903 is a heterologous expression construct that contains an yfp gene expression cassette (SEQ ID NO:3) and a pat gene expression construct (SEQ ID NO:4) is presented as a plasmid map in FIG. 1.

(provides the nucleic acid sequence for the yellow fluorescent protein gene expression cassette from pDAB113903)

SEQ ID NO: 3

```
caacaaaaatgcactttttcgccaaaaatacatttacttcaaaaaccgca
aaaatatttttctgccaaacccgtaaaaatactatttttctgccgaaacgt
aaaaaaaaatattttaattattttattaacaagtccacttggatgtagat
gaaaatttaaaaaatgaaaagcaaacgaacatagttgcattcagatgatt
catctggatgcatggacgaaatgaagaaacgaacaacacccatatagagc
atctggataagacatctagatggatcattacaaaagaacagggcctaaac
atgtgagatgtttgaagcaatcagtcaaaagtaaccaccaaatcgaatta
tgaaagcgttgattggatggacaagtttaacaaccattgtttgattggac
aacgccgttatctaaacttttagtgtgctgtgtacatcattactatgaat
cagttagttaaaaatattatggtcagtgaatgacagtaagattacttcag
aacttgagagatttaccgcaaaaagaaacacaataacgcgtaggaaaaat
atcctctgattttgcaattattctcgtagatttggttatcagtaggtatc
acgttttacaaaaatagaattacaatacatgccgcaagaaaaagactact
ctttttaatttccccaatttggttatcagtattcagtaagtttcacattt
ttacaaaaatataaattaaaatacatactgcaagaaaaatactttttttaa
tttcgccaatttggttatcagtagttttcacatttttacaaaaatataat
taaaatataaactgcaacaaaaagacttatattttaatttccccaatttg
gttatcagtattcagtaggtttcacatttacaaaaatattattaaaatac
atactgcaagaaacatacctttttaatttcgccaatctggttatcagtag
ttttcacatttttacaaaaatagaattaaaatacaaactgcaacaaaaag
acttatattttaatttccaccaataagttatttatttatttaatcctccc
gtgaggaaaaagacaagattgaggatgaatatacgtaactgaaaattgag
gaaacagagccatcaacattcaacacggatgatcatcatcatcactctct
gccgcattaaatagaaaccaacaaagacattcttgagcccacactcactc
attcctatttcttcgctttgcgtgccttccttccacttatctacttgtat
cccacaaaaagctacttaataccatttaataaagaccccaactttcttgt
gtcttctctcttatcatcttcgctgtgatctctctgtctccctctctctt
```

atccaaaagattagtataaaaggatcgatattccttgtgggacttccata
aaacttcgattctcgactggatctccatgtcatctggagcacttctattc
atgggaagattccttacgttgtggagatggaagggaatgttgatggccac
acattagcatacgtgggaaaggctacggagatgcctcagtgggaaaggta
tgatctgcttctacctttgatatatatataataattatcactaattagta
gtaatatagtatttcaagtatttttttcaaaataaaagaatgtagtatat
agctattgcttttctgtagatataagtgtgtatattttaatttataacta
tctaatatatgaccaaaacatggtgatgtgcaggttgatgcacaattcat
ctgtactaccggagatgttcctgtgccttggagcacacttgtcaccactc
tcacctatggagcacagtgattgccaagtatggtccagagttgaaggact
tctacaagtcctgtatgccagatggctatgtgcaagagcgcacaatcacc
tttgaaggagatggcaacttcaagactagggctgaagtcacctttgagaa
tgggtctgtctacaatagggtcaaactcaatggtcaaggcttcaagaaag
atggtcacgtgttgggaaagaacttggagttcaacttcactccccactgc
ctctacatctggggagaccaagccaaccacggtctcaagtcagccttcaa
gatatgtcatgagattactggcagcaaaggcgacttcatagtggctgacc
acacccagatgaacactcccattggtggaggtccagttcatgttccagag
tatcatcatatgtcttaccatgtgaaactttccaaagatgtgacagacca
cagagacaacatgagcttgaaagaaactgtcagagctgttgactgtcgca
agacctacctttgagtagttagcttaatcacctagagctcggtcaccact
ttactattctctctaatcgctcaatatacaaaagaaaagtgtttacatac
acacatcatatatagtttgatttagatccatgtaaccgaacgggtctgtt
tacttctatgaataaaatagctagttgatgattctgttgattgatacact
ctatggatagttcaagatttattacaatccaacgatgatttgtatcaaa
tagagcccaccagatcaagaaagcatactccagaagatttgttcaatcta
ccatcagataacatatcaataaccatcttcatggtggaaccatctgcagc
aaacccacacctcttcatttcttctatgagttcaactgaagcgactacac
cactacctccgagatgaactcggatcagtgtgttgtatgtacactcattt
ggcgcaatcccatcctcctctcccatctttttaaacaacatatccgcttc
agacagtgagcattcttacacagtcctgcaatcattatggta.

(provides the nucleic acid sequence for the phosphinothricin acetyl transferase gene expression cassette from pDAB113903)

SEQ ID NO: 4 ccagaaggtaattatccaagatgtagcatcaagaatccaatgtttacggg
aaaaactatggaagtattatgtaagctcagcaagaagcagatcaatatgc
ggcacatatgcaacctatgttcaaaaatgaagaatgtacagatacaagat
cctatactgccagaatacgaagaagaatacgtagaaattgaaaaagaaga
accaggcgaagaaaagaatcttgaagacgtaagcactgacgacaacaatg
aaaagaagaagataaggtcggtgattgtgaaagagacatagaggacacat
gtaaggtggaaaatgtaagggcggaaagtaaccttatcacaaaggaatct
tatcccccactacttatcatttatatttttccgtgtcatttttgcccttg
agttttcctatataaggaaccaagttcggcatttgtgaaaacaagaaaaa
atttggtgtaagctattttctttgaagtactgaggatacaacttcagaga
aatttgtaagtttgtaggtaccagatctggatcccaaaccatgtctccgg
agaggagaccagttgagattaggccagctacagcagctgatatggccgcg
gtttgtgatatcgttaaccattacattgagacgtctacagtgaactttag
gacagagccacaaacaccacaagagtggattgatgatctagagaggttgc
aagatagataccatggttggttgctgaggagagggtgttgtggctggtat
tgcttacgctgggccctggaaggctaggaacgcttacgattggacagttg
agagtactgtttacgtgtcacataggcatcaaaggttgggcctaggatct
acattgtacacacatttgcttaagtctatggaggcgcaaggtataagtct
gtggttgctgttataggccttccaaacgatccatctgttaggttgcatga
ggctttgggatacacagcccggggtacattgcgcgcagctggatacaagc
atggtggatggcatgatgttggttatggcaaagggattttgagttgccag
ctcctccaaggccagttaggccagttacccaaatctgagtagttagctta
atcacctagagctcgatcggcggcaatagcttcttagcgccatcccgggt
tgatcctatctgtgttgaaatagttgcggtgggcaaggctctctttcaga
aagacaggcggccaaaggaacccaaggtgaggtgggctatggctctcagt
tccttgtggaagcgcttggtctaaggtgcagaggtgttagcgggatgaag
caaaagtgtccgattgtaacaagatatgttgatcctacgtaaggatatta
aagtatgtattcatcactaatataatcagtgtattccaatatgtactacg
atttccaatgtctttattgtcgccgtatgtaatcggcgtcacaaaataat
ccccggtgactttcttttaatccaggatgaaataatatgttattataatt
tttgcgatttggtccgttataggaattgaagtgtgcttgaggtcggtcgc
caccactcccatttcataattttacatgtatttgaaaaataaaaatttat
ggtattcaatttaaacacgtatacttgtaaagaatgatatcttgaaagaa
atatagtttaaatatttattgataaaataacaagtcaggtattatagtcc
aagcaaaaacataaatttattgatgcaagtttaaattcagaaatatttca
ataactgattatatcagctggtacattgccgtagatgaaagactgagtgc
gatattatggtgtaatacatagg.

A positive control construct, pDAB9381, was assembled containing a yellow fluorescent protein (yfp) gene expression cassette, and a phosphinothricin acetyltransferase gene expression cassette. Specifically, the yellow fluorescent protein gene expression cassette contains the *Arabidopsis thaliana* Ubiquitin 10 gene promoter (At Ubil0 promoter; Callis et al., 1990, *J Biol Chem* 265:12486-12493), *yellow fluorescence protein* coding sequence (PhiYFP; Shagin et al., 2004 *Molecular Biology and Evolution*, 21(5), 841-850) which contains the *Solanum tuberosum*, light specific tissue inducible LS-1 gene (ST-LS1 intron; Genbank Acc No. X04753), and is terminated with the *Agrobacterium tumefaciens* Open Reading Frame 23 3' Untranslated Region (AtuORF23 3'UTR). The selectable marker gene expression cassette contains the Cassava vein Mosaic Virus Promoter (CsVMV promoter; Verdaguer et al., *Plant Molecular Biology* 31:1129-1139; 1996), phosphinothricin acetyl transferase (PAT; Wohlleben et al., *Gene* 70:25-37; 1988) and *Agrobacterium tumefaciens* ORF1 3' untranslated region (AtuORF1 3' UTR; Huang et al., J. Bacteriol. 172:1814-

Figure 2:
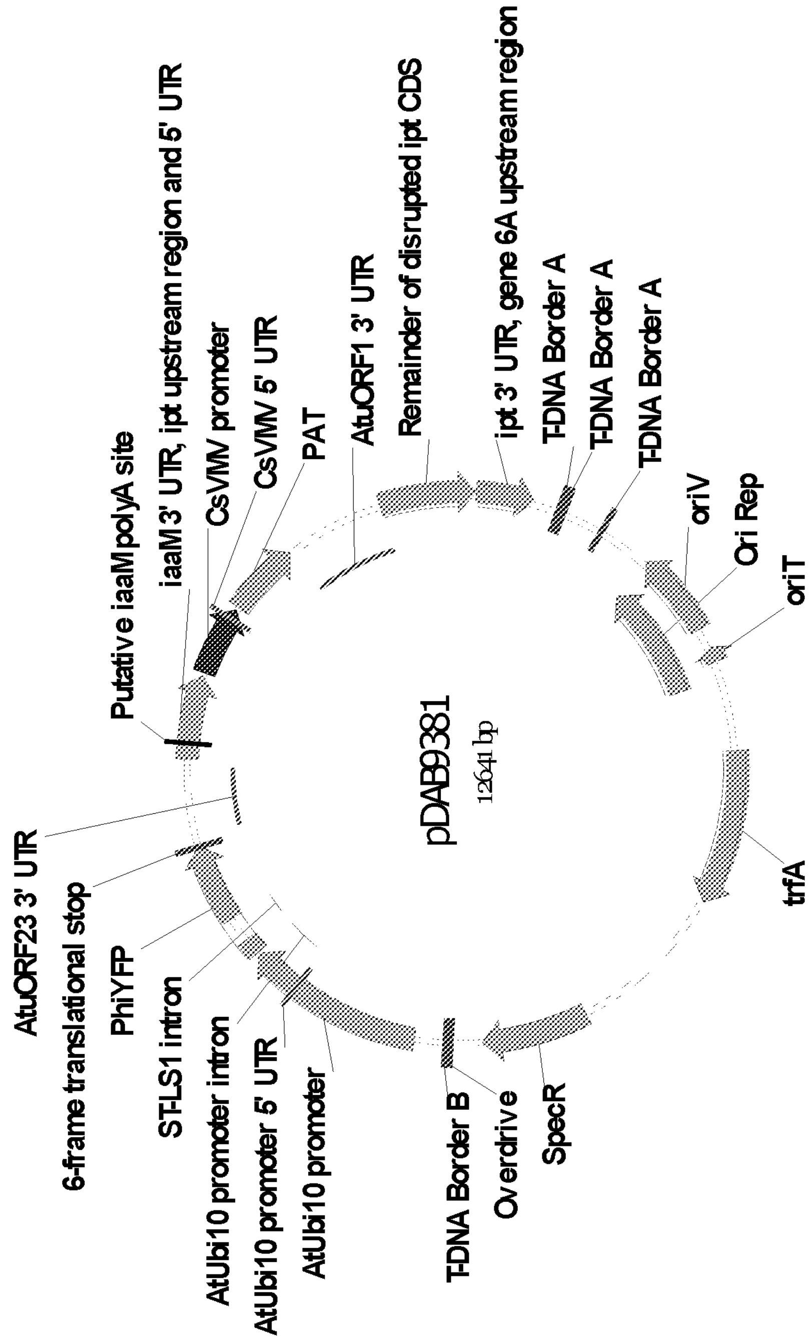
FIG. 2 shows a plasmid map of pDAB9381.

1822; 1990). The resulting construct, pDAB9381 is a heterologous expression construct that contains an yfp gene expression cassette (SEQ ID NO:5) and a pat gene expression construct (SEQ ID NO:5) is presented as FIG. 2.

(provides the nucleic acid sequence for the yellow fluorescent protein gene expression cassette from pDAB9381)

SEQ ID NO: 5

```
gtcgacctgcaggtcaacggatcaggatattcttgtttaagatgttgaac
tctatggaggtttgtatgaactgatgatctaggaccggataagttccatc
ttcatagcgaacttattcaaagaatgattgtgtatcattcttgttacatt
gttattaatgaaaaaatattattggtcattggactgaacacgagtgttaa
atatggaccaggccccaaataagatccattgatatatgaattaaataaca
agaataaatcgagtcaccaaaccacttgcatttttaacgagacttgttca
ccaacttgatacaaaagtcattatcctatgcaaatcaataatcatacaaa
aatatccaataacactaaaaaattaaaagaaatggataatttcacaatat
gttatacgataaagaagttacttttccaagaaattcactgattttataag
cccacttgcattagataaatggcaaaaaaaaacaaaaaggaaaagaaata
aagcacgaagaattctagaaaatacgaaatacgcttcaatgcagtgggac
ccacggttcaattattgccaattttcagctccaccgtatatttaaaaaat
aaaacgataatgctaaaaaaatataaatcgtaacgatcgttaaatctcaa
cggctggatcttatgacgaccgttagaaattgtggttgtcgacgagtcag
taataaacggcgtcaaagtggttgcagccggcacacacgagtcgtgttta
tcaactcaaagcacaaatacttttcctcaacctaaaaataaggcaattag
ccaaaaacaactttgcgtgtaaacaacgctcaatacacgtgtcattttat
tattagctattgcttcaccgccttagctttctcgtgacctagtcgtcctc
gtcttttcttcttcttcttctataaaacaatacccaaagcttcttcttca
caattcagatttcaatttctcaaaatcttaaaaactttctctcaattctc
tctaccgtgatcaaggtaaatttctgtgttccttattctctcaaaatctt
cgattttgttttcgttcgatcccaatttcgtatatgttctttggtttaga
ttctgttaatcttagatcgaagacgattttctgggtttgatcgttagata
tcatcttaattctcgattagggtttcataaatatcatccgatttgttcaa
ataatttgagttttgtcgaataattactcttcgatttgtgatttctatct
agatctggtgttagtttctagtttgtgcgatcgaatttgtcgattaatct
gagtttttctgattaacagagatctccatgtcatctggagcacttctctt
tcatgggaagattccttacgttgtggagatggaagggaatgttgatggcc
acacctttagcatacgtgggaaaggctacggagatgcctcagtgggaaag
gtatgtttctgcttctacctttgatatatatataataattatcactaatt
agtagtaatatagtatttcaagtatttttttcaaaataaaagaatgtagt
atatagctattgcttttctgtagtttataagtgtgtatattttaatttat
aacttttctaatatatgaccaaaacatggtgatgtgcaggttgatgcaca
attcatctgtactaccggagatgttcctgtgccttggagcacacttgtca
ccactctcacctatggagcacagtgctttgccaagtatggtccagagttg
aaggacttctacaagtcctgtatgccagatggctatgtgcaagagcgcac
```

-continued

```
aatcacctttgaaggagatggcaacttcaagactagggctgaagtcacct
ttgagaatgggtctgtctacaatagggtcaaactcaatggtcaaggcttc
aagaaagatggtcacgtgttgggaaagaacttggagttcaacttcactcc
ccactgcctctacatctggggagaccaagccaaccacggtctcaagtcag
ccttcaagatatgtcatgagattactggcagcaaaggcgacttcatagtg
gctgaccacacccagatgaacactcccattggtggaggtccagttcatgt
tccagagtatcatcatatgtcttaccatgtgaaactttccaaagatgtga
cagaccacagagacaacatgagcttgaaagaaactgtcagagctgttgac
tgtcgcaagacctacctttgagtagttagcttaatcacctagagctcggt
caccagcataatttttattaatgtactaaattactgttttgttaaatgca
attttgctttctcgggattttaatatcaaaatctatttagaaatacacaa
tattttgttgcaggcttgctggagaatcgatctgctatcataaaaattac
aaaaaaattttatttgcctcaattattttaggattggtattaaggacgct
taaattatttgtcgggtcactacgcatcattgtgattgagaagatcagcg
atacgaaatattcgtagtactatcgataatttatttgaaaattcataaga
aaagcaaacgttacatgaattgatgaaacaatacaaagacagataaagcc
acgcacatttaggatattggccgagattactgaatattgagtaagatcac
ggaatttctgacaggagcatgtcttcaattcagcccaaatggcagttgaa
atactcaaaccgccccatatgcaggagcggatcattcattgtttgtttgg
ttgcctttgccaacatgggagtccaaggtt
```

(provides the nucleic acid sequence for the phosphinothricin acetyl transferase gene expression cassette from pDAB9381)

SEQ ID NO: 6

```
ccagaaggtaattatccaagatgtagcatcaagaatccaatgtttacggg
aaaaactatggaagtattatgtaagctcagcaagaagcagatcaatatgc
ggcacatatgcaacctatgttcaaaaatgaagaatgtacagatacaagat
cctatactgccagaatacgaagaagaatacgtagaaattgaaaaagaaga
accaggcgaagaaaagaatcttgaagacgtaagcactgacgacaacaatg
aaaagaagaagataaggtcggtgattgtgaaagagacatagaggacacat
gtaaggtggaaaatgtaagggcggaaagtaaccttatcacaaaggaatct
tatcccccactacttatccttttatatttttccgtgtcatttttgccctt
gagttttcctatataaggaaccaagttcggcatttgtgaaaacaagaaaa
aatttggtgtaagctattttctttgaagtactgaggatacaacttcagag
aaatttgtaagtttgtaggtaccagatctggatcccaaaccatgtctccg
gagaggagaccagttgagattaggccagctacagcagctgatatggccgc
ggtttgtgatatcgttaaccattacattgagacgtctacagtgaacttta
ggacagagccacaaacaccacaagagtggattgatgatctagagaggttg
caagatagatacccttggttggttgctgaggagagggtgttgtggctggt
attgcttacgctgggccctggaaggctaggaacgcttacgattggacagt
tgagagtactgtttacgtgtcacataggcatcaaaggttgggcctaggat
ctacattgtacacacatttgcttaagtctatggaggcgcaaggtataagt
```

-continued

```
ctgtggttgctgttataggccttccaaacgatccatctgttaggttgcat
gaggctttgggatacacagcccggggtacattgcgcgcagctggatacaa
gcatggtggatggcatgatgttggttatggcaaagggattttgagttgcc
agctcctccaaggccagttaggccagttacccaaatctgagtagttagct
taatcacctagagctcgatcggcggcaatagcttcttagcgccatcccgg
gttgatcctatctgtgttgaaatagttgcggtgggcaaggctctctttca
gaaagacaggcggccaaaggaacccaaggtgaggtgggctatggctctca
gttccttgtggaagcgcttggtctaaggtgcagaggtgttagcgggatga
agcaaaagtgtccgattgtaacaagatatgttgatcctacgtaaggatat
taaagtatgtattcatcactaatataatcagtgtattccaatatgtacta
cgatttccaatgtctttattgtcgccgtatgtaatcggcgtcacaaaata
atccccggtgactttcttttaatccaggatgaaataatatgttattataa
tttttgcgatttggtccgttataggaattgaagtgtgcttgaggtcggtc
gccaccactcccatttcataattttacatgtatttgaaaaataaaaattt
atggtattcaatttaaacacgtatacttgtaaagaatgatatcttgaaag
aaatatagtttaaatatttattgataaaataacaagtcaggtattatagt
ccaagcaaaaacataaatttattgatgcaagtttaaattcagaaatattt
caataactgattatatcagctggtacattgccgtagatgaaagactgagt
gcgatattatggtgtaatacatagg
```

Example 4

Plant Transformation and Molecular Confirmation

*Agrobacterium* Preparation

Next, 60 μl of an *Agrobacterium* strain, in 50% glycerol (previously prepared and frozen at −80° C.), containing either one of the above described binary plasmids, was used to prepare a 5 ml starter culture of YEP liquid (BACTO PEPTONE™ 10.0 gm/L, Yeast Extract 10.0 gm/L, and sodium chloride 5.0 gm/L) containing spectinomycin (100 mg/L), kanamycin (50 mg/L), and rifampicin (10 mg/L) and incubated for overnight at 28° C. with aeration. The *Agrobacterium* starter was then inoculated into 300 mL YEP liquid with spectinomycin (100 mg/L), kanamycin (50 mg/L), and rifampicin (10 mg/L) into sterile 500 mL baffled flask(s) and shaken at 200 rpm at 28° C. overnight. The cultures were centrifuged at 6000 rpm and resuspended in an equal volume of ½×MS-medium containing 10% (w/v) sucrose, 10 ug/L 6-benzylaminopurine, and 0.03% Silwet L-77 prior to transformation of plant tissue.

*Arabidopsis* Transformation

*Arabidopsis* was transformed using the floral dip method adapted from Clough and Bent (1998). A validated *Agrobacterium* glycerol stock containing one of the binary plasmids described above was used to inoculate a 5 mL preculture of YEP broth containing spectinomycin (100 mg/L), kanamycin (50 mg/L), and rifampicin (10 mg/L). The culture was incubated overnight at 28° C. with aeration. The pre-culture was then bulked up to 300 mL with the same antibiotic selection and incubated again at 28° C. with constant agitation at 225 rpm. The cells were pelleted at approximately 5,000×g for 15 minutes at 4° C., and the supernatant discarded. The cell pellet was gently resuspended in 300 mL inoculation medium containing: 10% (w/v) sucrose, 10 ug/L 6-benzylaminopurine, and 0.03% Silwet L-77. Plants at 41 days old (primary inflorescences cut back at 35 days) were inverted and dipped into the medium. The plants (now denoted as $T_0$) were placed on their sides in a transparent covered plastic tub overnight, and then set upright in the growth chamber the following day. The plants were grown at 22° C., with a 16-hour light/8-hour dark photoperiod. Four weeks after dipping, the water was cut off and plants were allowed to dry down for a week in preparation for $T_1$ seed harvesting.

$T_1$ seed was sown on 10.5"×21" germination trays, each receiving a 200 mg aliquots of stratified $T_1$ seed (~10,000 seed) that had previously been suspended in 40 mL of 0.1% agar solution and stored at 4° C. for 2 days to ensure synchronous seed germination (vernalization).

Sunshine Mix LP5 soil media was covered with fine vermiculite and subirrigated with Hoagland's solution until wet, then allowed to gravity drain. Each 40 mL aliquot of stratified seed was sown evenly onto the vermiculite with a pipette and covered with humidity domes for 4-5 days. Domes were removed 1 day prior to initial transformant selection using glufosinate (Liberty).

Seven days after planting (DAP) and again at 9 DAP, $T_1$ plants (cotyledon and 2-4-1f stage, respectively) were sprayed with a 0.2% solution of Liberty herbicide (200 g ai/L glufosinate, Bayer Crop Sciences, Kansas City, Mo.) at a spray volume of 10 ml/tray (703 L/ha) using a DeVilbiss compressed air spray tip to deliver an effective rate of 280 g ai/ha glufosinate per application. Survivors (putative transformed plants actively growing) were identified 3 days after the final spraying and transplanted individually into 3-inch pots prepared with Sunshine Mix LP5 in the greenhouse 7 days after the final spray selection (16 DAP). The transplants were reared in the greenhouse (22±5° C., 50±30% RH, 14 h light:10 dark, minimum 500 $\mu E/m^2s^1$ natural+supplemental light). Molecular analysis was completed on the surviving $T_1$ plants to confirm that the pat herbicide selectable marker gene had integrated into the genome of the plants.

Molecular Confirmation

Putative transgenic *Arabidopsis* plants were sampled for detection of transgene presence using a quantitative PCR assay for pat. Total DNA was extracted from the leaf samples, using QIAGEN® BioSprint96 Kit DNA extraction kit (Qiagen, Valencia, Calif.) as per manufacturer's instructions.

To detect the genes of interest, gene-specific DNA fragments were amplified with hydrolysis (analogous to TAQMAN®) primer/probe sets containing a Cy5-labeled fluorescent probe for the pat gene and a HEX-labeled fluorescent probe for the endogenous TafII-15 reference gene control (Genbank ID: NC 003075; Duarte et al., *BMC Evol. Biol.,* 10:61). The following primers were used for the pat and endogenous TafII-15 reference gene amplifications. The primer sequences were as follows:

```
pat Primers/Probes:
Pat Forward Primer:
                                        (SEQ ID NO: 7)
TQPATS:ACAAGAGTGGATTGATGATCTAGAGAGGT

Pat Reverse Primer:
                                        (SEQ ID NO: 8)
TQPATA: CTTTGATGCCTATGTGACACGTAAACAGT
```

-continued

```
Pat Probe:
                                          (SEQ ID NO: 9)
5'-/5Cy5/AGGGIGTTGIGGCTGGTATTGCTTACGCT/3BHQ2/-3'

TafII-15 Primers/Probes:
Forward Primer: TafII-15 F:
                                          (SEQ ID NO: 10)
GAGGATTAGGGTTTCAACGGAG

Reverse Primer: TafII-15 R:
                                          (SEQ ID NO: 11)
GAGAATTGAGCTGAGACGAGG

TafII-15 Probe:
                                          (SEQ ID NO: 12)
5'-/5HEX/AGAGAAGITTCGACGGATTTCGGGC/3BHQ2/-3'
```

Next, the qPCR reactions were carried out in a final volume of 10 μl reaction containing 5 μl of Roche LIGHTCYCLER® 480 Probes Master Mix (Roche Applied Sciences, Indianapolis, Ind.); 0.4 μl each of TQPATA, TQPATS, TafII-15 F and TafII-15 R primers from 10 μM stocks to a final concentration of 400 nM; 0.4 μl each of Pat Probe and TafII-15 Probe from 5 μM stocks to a final concentration of 200 nM, 2 μl of genomic DNA diluted 1:5 in water, and 0.5 μl water. The DNA was amplified in a Roche LIGHTCYCLER® 480 System under the following conditions: 1 cycle of 95° C. for 10 min followed by 40 cycles of the following 3-steps: 95° C. for 10 seconds; 60° C. for 40 seconds and 72° C. for 1 second. The pat copy number was determined by comparison of Target (gene of interest)/Reference (Invertase gene) values for unknown samples (output by the LIGHTCYCLER® 480) to Target/Reference values of pat copy number controls.

From the molecular confirmation, specific *Arabidopsis* transgenic events that contained a single transgene insert of the above described plasmids were identified. These plants were self-fertilized, and the resulting $T_1$ seed was planted to monitor and assay $T_1$ seedlings for YFP protein expression in different plant tissues at different developmental stages.

Example 5

Transgenic Plant Expression Screening

The *Arabidopsis* $T_1$ transgenic events were grown into seedlings and assessed for YFP fluorescence at 15 DAP via fluorescent microscopy and visual observation. Additional, observation of the *Arabidopsis* $T_1$ transgenic events was completed a 7 weeks after planting, wherein the leaves, inflorescences and siliques were viewed via fluorescent microscopy and visual observation. Finally, observation of the *Arabidopsis* $T_1$ transgenic events was completed a 10 weeks after planting, wherein the developing seedlings were viewed via fluorescent microscopy and visual observation. Seedlings and developing seeds were imaged using a Leica DFC310 FX Stereoscope™ (Leica, Buffalo Grove, Ill.) with the following settings (e.g., excitation max—525 nm and emission max—482 nm). Leaves, inflorescences and siliques were imaged using the TYPHOON SCANNER™ (GE Healthcare Life Sciences, Piscataway, N.J.) with the following settings (e.g., Blue 488 nm laser, 670 BP 30 for chllorophyll, 520 BP 40 for Phiyfp, 350 PMT).

Figure 3:
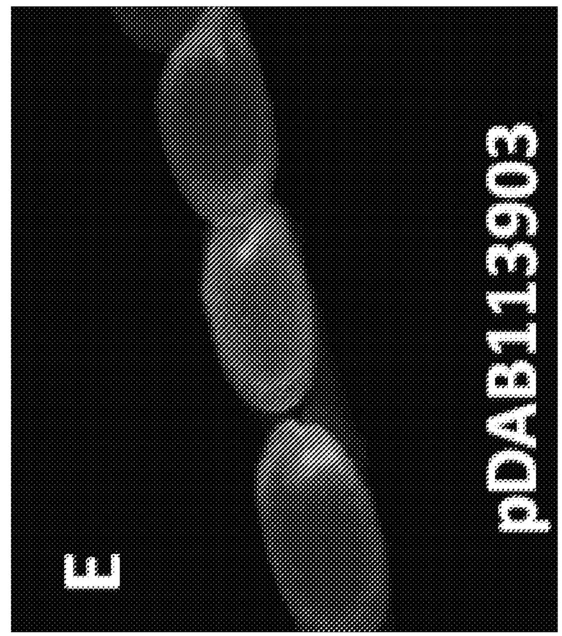
FIG. 3 is a microscopy image of Yellow Fluorescent Protein expression patterns in transgenic *Arabidopsis* plant tissues. The image provided in Panel D shows early ovule expression that was localized in the endosperm for the YFP protein, driven by the *Brassica napus* GALE1 promoter and terminated by 3' UTR regulatory elements as described in pDAB113903. The image provided in Panel E shows expression of the YFP protein, driven by the *Brassica napus* GALE1 promoter and terminated by 3' UTR regulatory elements as described in pDAB113903, in other plant tissues such as roots, petioles and flowers. The expression of the YFP protein in the root, petiole and flower tissue was observed in multi-copy number events.
Figure 3:
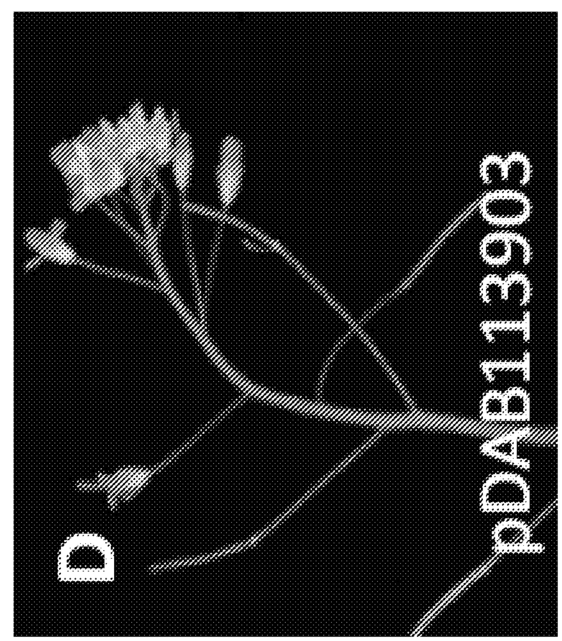

The YFP imaging of $T_1$ seedlings and plant tissues indicated that seed preferential expression of the protein expressed under the control of the *Brassica napus* GALE1 gene promoter and terminated by the *Brassica napus* GALE1 gene 3' UTR was detected in single copy events. Visual observations suggest that expression driven by these regulatory elements is specific to early seed development, and early floral development. As such, the expression pattern driven by the *Brassica napus* GALE1 regulatory elements was observed within the ovules of developing inflorescences (FIG. 3). The expression of the YFP protein tissue is most likely localized within endosperm tissues during the development of seed within *Arabidopsis* plants. The expression in the endosperm tissue is significant, as this tissue type makes up the majority of seed tissues during early seed development. Further expression of the YFP protein was observed in the flowers, stems, leaves, and seeds of transgenic events containing multiple copies of the yfp transgene.

Example 6

Expression Protein Quantification in *Arabidopsis*

Samples of the *Arabidopsis* plant seeds were assayed via PhiYFP ELISA seeds were collected and subjected to bead-milling. About 10 mg of seed material was beat with 2 BBs (4.5 mm steel balls; Daisy; Rogers, Ark.) for 1 minute in a KLECCO™ bead mil 300 μl of extraction buffer (PBS supplemented with 0.05% Tween20 and 0.05% bovine serum albumin was added. The samples were suspended with gentle tapping and rocked on a platform shaker for 30 minutes at room temperature. The samples were then spun down in a centrifuge at 14,000×g for 5 minutes. The supernatant was removed and analyzed via ELISA. Maxisorb Plates™ (Thermo Fisher Scientific) were coated with an anti-YFP monoclonal antibody (Origene #TA150028) at a concentration of 1.0 μg/ml in 1×PBS. Following overnight incubation at 4° C., plates were blocked with PBST (PBS+0.5% TWEEN®-20) with 0.5% bovine serum albumin for 2 hours at 37° C. Prior to analysis, plates were washed 4 times in a plate washer using 350 μl of PBST per wash. A purified protein reference antigen (Evrogen) was diluted in blocking buffer to 2 ng/ml and used to generate a standard curve of serial dilutions from 2 ng/ml to 0.0313 ng/ml. Samples were diluted in blocking buffer to a starting dilution of 1:4 and diluted at a 1:4 rate 3 additional times (1:4, 1:16, 1:64, 1:256). Next, 100 μl of all standards and sample dilutions were loaded in duplicate onto the ELISA plate. Samples were incubated on the ELISA plate at room temperature for 1 hour. Following incubation, the plate was washed as above. A rabbit anti-PhiYFP polyclonal antibody (Evrogen) was diluted to 1 μg/ml in blocking buffer and added to the plate at 100 μl per well. The plate was incubated at room temperature for 1 hour prior to washing. An anti-rabbit horseradish peroxidase conjugated detection antibody (Pierce) was added to the plate at a 1:5000 dilution. The plate was incubated at room temperature for 1 hour and washed as above. Next, 1-Step Ultra TMB Substrate™ (Thermo Scientific) was added to the plate at 100 μl per well. As the wells with the lowest dilution of the standard curve began to show blue color, the reaction was stopped by adding 50 μl of stop solution (0.4 N H2SO4). The plate was read in a plate reader (Molecular Devices) using SOFTMAX® Pro v5 (Molecular Devices) at a wavelength of 450 nm minus a 650 nm reference. The PhiYFP concentration of test samples was calculated by linear regression of a quadratic standard curve.

The expression levels of YFP were quantitated and are provided in Table 1 below. The expression of YEP by the *Brassica napus* GALE1 regulatory elements ranged from 0.018 to 0.070 ng/mg within the *Arabidopsis* seed for the transgenic events containing low copy number events (i.e., 1-2 copies). Furthermore, the results indicated that the average expression of the low copy number event was about 0,047 ng/mg. Finally, expression of YFP by the *Brassica napus* GALE1 regulatory elements was 6.341 ng/mg within the seed of *Arabidopsis* for the transgenic events containing high copy number events (i.e., more than 2 copies),

TABLE 1

Quantitated expression of YFP in *Arabidopsis* seed.

| Seed Name | PAT copy number | YFP copy number | Expression of YFP ng/mg seed | Average Expression ng/mg seed |
|---|---|---|---|---|
| 113903[2]-004.sx001. | 0.98 | 0.92 | 0.018 | 0.047 ng/mg for single copy events |
| 113903[2]-017.sx001. | 0.93 | 0.86 | 0.047 | |
| 113903[2]-019.sx001. | 1.04 | 0.86 | 0.070 | |
| 113903[2]-034.sx001. | 0.98 | 0.84 | 0.053 | |
| 113903[2]-023.sx001. | 7.02 | 6.2 | 6.341 | 6.341 ng/mg for multiple copy events |
| Wt Negative | 0.00 | 0.00 | 0.000 | 0.0000 |
| Wt Negative | 0.00 | 0.00 | 0.000 | |

As such, *Brassica napus* GALE1 gene regulatory elements were identified and characterized. Disclosed for the first time are novel promoter and 3'-UTR regulatory elements for use in gene expression constructs.

We claim:

1. A gene expression cassette comprising a promoter operably linked to a heterologous coding sequence, wherein the promoter comprises a polynucleotide that has at least 98% sequence identity to SEQ ID NO:1, and wherein the promoter drives expression of the heterologous coding sequence.

2. The gene expression cassette of claim 1, wherein the polynucleotide comprises an intron.

3. The gene expression cassette of claim 1, wherein the polynucleotide comprises a 5'-untranslated region.

4. A recombinant vector comprising the gene expression cassette of claim 1.

5. A transgenic cell comprising the gene expression cassette of claim 1.

6. The transgenic cell of claim 5, wherein the promoter comprises SEQ ID NO:1.

7. The transgenic cell of claim 5, wherein the polynucleotide comprises a 5'-untranslated region.

8. The transgenic cell of claim 5, wherein the transgenic cell is a transgenic plant cell.

9. A transgenic plant comprising the transgenic cell of claim 8.

10. The transgenic plant of claim 9, wherein the plant is selected from the group consisting of an *Arabidopsis* plant, a tobacco plant, a soybean plant, a canola plant and a cotton plant.

11. A transgenic seed from the transgenic plant of claim 9.

12. The transgenic cell of claim 5, wherein the promoter consists of a polynucleotide sequence of nucleotides 1-820 of SEQ ID NO:1.

13. The gene expression cassette of claim 1, wherein the promoter consists of a polynucleotide sequence of nucleotides 1-1429 of SEQ ID NO:1.

14. The gene expression cassette of claim 1, wherein the heterologous coding sequence is operably linked to a 3'-untranslated region.

15. A recombinant vector comprising the gene expression cassette of claim 14.

16. A transgenic cell comprising the gene expression cassette of claim 14.

17. The transgenic cell of claim 16, wherein the transgenic cell is a transgenic plant cell.

18. A transgenic plant comprising the transgenic plant cell of claim 17.

19. The transgenic plant of claim 18, wherein the plant is selected from the group consisting of an *Arabidopsis* plant, a tobacco plant, a soybean plant, a canola plant and a cotton plant.

20. A transgenic seed from the transgenic plant of claim 18.

* * * * *